United States Patent
Li et al.

(10) Patent No.: US 9,375,457 B2
(45) Date of Patent: Jun. 28, 2016

(54) **COMPOSITION COMPRISING *RHIZOMA COPTIDIS*, *CORTEX PHELLODENDRI* AND *FRUCTUS GARDENIAE* AND FOR TREATING NEURODEGENERATIVE DISEASES**

(71) Applicant: Hong Kong Baptist University, Hong Kong (HK)

(72) Inventors: Min Li, Hong Kong (HK); Siva Sundara Kumar Durairajan, Hong Kong (HK); Lei Lei Chen, Hong Kong (HK); Liang Feng Liu, Hong Kong (HK); Ju Xian Song, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 128 days.

(21) Appl. No.: 14/303,622

(22) Filed: Jun. 13, 2014

(65) Prior Publication Data

US 2014/0370134 A1 Dec. 18, 2014

Related U.S. Application Data

(60) Provisional application No. 61/834,437, filed on Jun. 13, 2013, provisional application No. 61/836,118, filed on Jun. 17, 2013.

(51) Int. Cl.
| | | |
|---|---|---|
| *A01N 65/00* | (2009.01) | |
| *A61K 36/718* | (2006.01) | |
| *A61K 36/756* | (2006.01) | |
| *A61K 36/744* | (2006.01) | |
| *A61K 31/4745* | (2006.01) | |
| *A61K 31/7048* | (2006.01) | |

(52) U.S. Cl.
CPC ........... *A61K 36/718* (2013.01); *A61K 31/4745* (2013.01); *A61K 31/7048* (2013.01); *A61K 36/744* (2013.01); *A61K 36/756* (2013.01)

(58) Field of Classification Search
CPC ....................................................... A61K 36/00
USPC .......................................................... 424/725
See application file for complete search history.

(56) References Cited

FOREIGN PATENT DOCUMENTS

| CN | 1142378 A | 2/1997 |
| CN | 1644206 A | 7/2005 |
| CN | 102106943 A | 6/2011 |
| CN | 102512590 A | 6/2012 |

OTHER PUBLICATIONS

Li Yi, Xu Xu, Study on the precipitation reaction between baicalin and berberine by HPL, Journal of Chromatography B, Aug. 13, 2004, pp. 165-168, vol. 810, Elsevier B.V.
Katherine Lynn Youmans, Steffi Leung, Juan Zhang, Erika Maus, Kathleen Baysaz, Guo Jun Bu, Robert Vassar, Chunjiang Yu, Mary Jo Ladu, Amyloid-β42 Alters Apolipoprotein E Solubility in Brains of Mice with Five Familial AD Mutations, J Neurosci Methods., Mar. 15, 2011, pp. 51-59, vol. 196 No. 1, Elsevier B.V.
Sang-Moon Yun, Sun-Jung Cho, Jae Chung Song, Sung Yeon Song, Sangmee Ahn Jo, Chulman Jo, Keejung Yoon, Rudolph E. Tanzi, Eui-Ju Choi, Young Ho Koh, SUMO1 modulates Aβ generation via BACE1 accumulation, Neurobiology of Aging, 2013, pp. 650-662, vol. 34, Elsevier.
Huawu Zeng, Shengshan Dou, Jing Zhao, Siyang Fan; Xing Yuan, Shuanglai Zhu, Li Li, Weidong Zhang, Runhui Liu, The inhibitory activities of the components of Huang-Lian-Jie-Du-Tang (HLJDT) on eicosanoid generation via lipoxygenase pathway, Journal of Ethnopharmacology, Apr. 2, 2011, p. 561-568, vol. 135, Elsevier Ireland Ltd.
She-Qing Zhang, Demian Obregon, Jared Ehrhart, Juan Deng, Jun Tian, Huayan Hou, Brian Giunta, Darrell Sawmiller and Jun Tan, Baicalein Reduces b-Amyloid and Promotes Nonamyloidogenic Amyloid Precursor Protein Processing in an Alzheimer's Disease Transgenic Mouse Model, Journal of Neuroscience Research, May 17, 2013, pp. 1239-1246, vol. 91, Wiley Periodicals, Inc.
Huaxu Zhu, Zhilei Qian, Feng He, Mengzhu Liu, Linmei Pan, Novel pharmacokinetic studies of the Chinese formula Huang-Lian-Jie-Du-Tang in MCAO rats, 2013, pp. 767-774, vol. 20, Phytomedicine, Elsevier GmbH.
Evidence Reports of Kampo Treatment Task Force for Evidence Reports / Clinical Practice Guideline Committee for EBM, the Japan Society for Oriental Medicine, "9. Cardiovascular Diseases".
Nahuai Badiola, Victor Alcalde, Albert Pujol, Lisa-Marie Mu Nters, Gerd Multhaup, Alberto Lleo, Mireia Coma, Monsterrat Soler Lo Pez, Patrick Aloy, The Proton-Pump Inhibitor Lansoprazole Enhances Amyloid Beta Production, Plos One, Mar. 8, 2013, pp. 1-8, vol. 8 issue 3, PLOS ONE.
Iryna Benilova, Eric Karran & Bart De Strooper, The toxic Aβ oligomer and Alzheimer's disease: an emperor in need of clothes, Nature Neuroscience, Jan. 29, 2012, pp. 349-357, vol. 15, No. 3, Nature America Inc, USA.
Dennis J. Selkoe, Cell biology of protein misfolding: The examples of Alzheimer's and Parkinson's diseases, Nature Cell Biology, Nov. 2004, pp. 1054-1061, vol. 6 No. 11, Nature Publishing Group.
Junhui Chen, Fengmei Wang, Jie Liu, Frank Sen-Chun Lee, Xiaoru Wang, Huanghao Yang, Analysis of alkaloids in Coptis chinensis Franch by accelerated solvent extration combined with utlra performance liquid chromatograhic analysis with photodiodie array and tandem mass spectrometry detections, Analytical Chimica Acta, Mar. 5, 2008, pp. 184-195, Elsevier.

(Continued)

*Primary Examiner* — Michael Meller
(74) *Attorney, Agent, or Firm* — Ella Cheong Hong Kong; Sam T. Yip

(57) ABSTRACT

This invention is in the field of pharmaceuticals, health supplements and chemical industries. In particular, this invention relates a herbal composition that compensates the Aβ increasing effects of existing treatment, and on the regulatory processing of amyloid-β protein precursor (APP), therefore presenting a significantly more potent treatment for neurodegenerative diseases that does not associate with any β-amyloid increasing effect.

10 Claims, 24 Drawing Sheets

(56) References Cited

OTHER PUBLICATIONS

Chen Guo Hua, Shan Ping, Qiu Xin, The Clinical Study on Huanglian jiedu Decoction on for patients with Senile Dementia, the Type of Hyperactivity of Heart—Fire and Liver Fire in TCM, JETCM, 2007, vol. 116, No. 4, p. 386-387 and p. 434.

Alessio Colombo, Antonio Bastone, Cristina Ploia, Alessandra Sclip, Mario Salmona, Gianluigi Forloni, Tiziana Borsello, JNK regulates APP cleavage and degradation in a model of Alzheimer's disease, Neurobiology of Disease, Jan. 8, 2000, pp. 518-525, vol. 33, Elsevier.

Edgar F. Da Cruz E Silva and Odete A.B. Da Cruz E Silva, Protein Phosphorylation and APP Metabolism, Neurothernioai Research, Oct. 2003, pp. 1553-1561,vol. 28, No. 10, Plenum Publishing Corporation.

Siva Sundara Kumar Durairajan, Liang-Feng Liu, Jia Hong Lu, Irene Koo, Kei Maruyama, Sookja K Chung, Jian Dong Huang and Min Li, Stimulation of Non-Amyloidogenic Processing of Amyloid-β Protein Precursor by Cryptotanshinone Involves Activation and Translocation of ADAM10 and PKC-α, Journal of Alzheimer's Disease, Feb. 8, 2011, pp. 245-262, vol. 25, IOS Press and the authors, Hong Kong.

Siva Sundara Kumar Durairajan, Liang-Feng Liu, Jia Hong Lu, Lei-Lei Chen, Qiuju Yuan,Sookja K Chung, Ling Huang, Xing-Shu Li, Jian Dong Huang and Min Li, Berberine ameliorates β-amyloid pathology gliosis, and cognitive impairment in an Alzheimer's disease transgenic mouse model, Neurobiology of Aging, Feb. 15, 2012, pp. 2903-2919, vol. 33, Elsevier.

John Hardy, Dennis J. Selkoe, The Amyloid Hypothesis of Alzheimer's Disease: Progress and Problems on the Road to Therapeutics, Science's Compass Review, Jul. 19, 2002, pp. 353-356, vol. 297, Science, USA.

Crtstak D. Hayes, Debleena Dey, Juan Pablo Palavicini, Hongjie Wang, Wataru Araki, Madepalli K. Lakshmana, Chronic Cladribine Administration Increases Amyloid Beta Peptide Generation and Plaque Burden in Mice, PLOS ONE, Oct. 3, 2012, pp. 19, vol. 7 issue 10, PLOS ONE.

Yaohua Hu, Peng Jiang, Shuping Wang, Shikai Yan, Li Xiang, Weidong Zhang and Runhui Liu, Plasma pharmacochemistry based approach to screening potential bioactive components in Huang-Lian-Jie-Du-Tang using high performance liquid chromatography coupled with mass spectrometric detection, Journal of Ethnopharmacology, Aug. 12, 2011, pp. 728-735, vol. 141, Elsevier.

Ko Ichi Iijima, Kanae Ando, Shizu Takeda, Yasushi Satoh, Tatsunori Seki, Shigeyoshi Itohara, Paul Greengard, Yutaka Kirino, Angus C. Nairn and Toshiharu Suzuki, Neuron-Specific Phosphorylation of Alzheimer's b-Amyloid Precursor Protein by Cyclin-Dependent Kinase 5 ,Journal of Neurochemistry, Apr. 18, 2000, pp. 1085-1091, vol. 75, No. 3, International Society for Neurochemistry.

Evidence Reports of Kampo Treatment 2010; Task Force for Evidence Reports/Clinical Practice Guideline Special Committee for EBM, the Japan Society for Oriental Medicine; Cardiovascular Diseases.

Ali Khoddami, Meredith A. Wilkes and Thomas H. Roberts, Techniques for Analysis of Plant Phenolic Compounds, Molecules, Feb. 19, 2013, pp. 2328-2375, vol. 18, Department of Plant and Food Sciences, University of Sydney, Sydney, NSW 2006, Australia.

Yoichi Kondo, Fumio Kondo, Masato Asanuma, Ken-Ichi Tanaka and Norio Ogawa, Protective Effect of Oren-gedoku-to Against Induction of Neuronal Death by Transient Cerebral Ischemia in the C57BL/6 Mouse, Neurochemical Research, 2000, pp. 205-209, vol. 25, No. 2, Plenum Publishing Corporation.

Frank M. Laferla, Kim N. Green and Salvatore Oddo, Intracellular amyloid-β in Alzheimer's disease, Nature Reviews, Jul. 2007,pp. 499-509, vol. 8, Nature Publishing Group.

Orly Lazarov, Gerardo A. Morfini, Edward B.Lee, Mohamed H. Farah, Anita Szodoral, Scott R. Deboer, Vassilis E. Koliatsos, Stefan Kins, Virginia M. -Y. Lee, Philip C. Wong, Donald L. Price, Scott T. Brady and Sangram S Slsodia, Axonal Transport, Amyloid Precursor Protein, Kinesin-1, and the Processing Apparatus: Revisited, The Journal of Neuroscience, Mar. 2, 2005, pp. 2386-2395, vol. 25 No. 9, Society for Neuroscience.

Ming Sum Lee, Shih Chu Kai, Cynthia A. Lemere, Weiming Xia, Huang Chun Tseng, Ying Zhou, Rachel Neve, Michael K. Ahlijanian, and Li-Huei Tsai, APP processing is regulated by cytoplasmic phospharylation, The Journal of Cell Biology, Oct. 13, 2003, pp. vol. 163 No. 1, The Rockefeller University Press.

Yu Li, Wei Hui Zhou, Yigang Tong, Guiqiong He and Weihong Song,Control of APP processing and A generation level by BACE1 enzymatic activity and transcription, The FASEB Journal, Feb. 2006, pp. 285-292, vol. 20, FASEB.

A. Lleo, S.M. Greenberg, and J.H. Growdon, Current Pharmacotherapy for Alzheimer's Disease, Annual Review of Medicine, Aug. 11, 2005, pp. 517-533, vol. 57, Annual Reviews.

Tong Lu, Jue Song, Fang Huang, Yuanxiong Deng, Lin Xie, Guangji Wang, Xiaodong Liu, Comparative pharmacokinetics of baicalin after oral administration of pure baicalin, Radix scutellariae extract and Huang-Lian-Jie-Du-Tang to rats, Journal of Ethnopharmacology,Oct. 13, 2006, pp. 412-418, vol. 110, Elsevier.

Jia-Hong Lu, Mustafa Taleb Ardah, Siva Sundara Kumar Durairajan, Liang-Feng Liu, Li Xia Xie, Wang-Fun David Fong, Mohamed Y. Hasan, Jian-Dong Huang, Omar M.A. El Agnaf and Min Li, Baicalein Inhibits Formation of a-Synuclein Oligomers within Living Cells and Prevents Ab Peptide Fibrillation and Oligomerisation, ChemBioChem, 2011, pp. 615-624, vol. 12, Wiley-VCH Verlag GmbH& Co. KGaA, Weinheim.

Jiun-Lung Luo, Fen-Ling Lu, Yi-Chu Liu and Chi-Fang Lo, Identification of Scutellaria Baicalensis in Traditional Chinese Medicine Preparations by LC/MS/MS Fingerprinting Method, Journal of Food and Drug Analysis, 2012, pp. 887-899, vol. 20, No. 4, Food and Drug Administration,Taiwan R.O.C.

Hideki Okamoto, Atsushi Chino, Yoshio Hirasaki, Keigo Ueda, Masaomi Iyo, Takao Namiki, Orengedoku-to augmentation in cases showing partial response to yokukan-san treatment: a case report and literature review of the evidence for use of these Kampo herbal formulae,Neuropsychiatric Disease and Treatment, Jan. 17, 2013, pp. 151-155, vol. 9, Dove Medical Press Ltd.

Daniel Paris, Nowell J Ganey, Vincent Laporte, Nikunj S Patel, David Beaulieu-Abdelahad, Corbin Bachmeier, Amelia March, Ghania Ait-Ghezala, Michael J Mullan, Reduction of b-amyloid pathology by celastrol in a transgenic mouse model of Alzheimer's disease, Journal of Neuroinflammation, 2010, pp. 1-15, Blomed Central , USA.

Lucia Pastorino, Anyang Sun, Pri-Jung Lu, Xiao Zhen Zhou, Martin Balastik, Greg Finn, Gerburg Wulf, Jormay Lim, Shi Hua Li, Xiaojiang Li, Weiming Xia, Linda K. Nicholson & Kun Ping Lu, The prolyl isomerase Pin1 regulates amyloid precursor protein processing and amyloid-b production, Nature, Mar. 23, 2006, pp. 528-534, vol. 440, Nature Publishing Group.

Y. Peng,D. Y. W. Lee, L. Jiang,Z. Ma, S. C. Schachter and C. A. Lemere, Huperzine a regulates amyloid precursor protein processing via protein kinase c and mitogen-activated protein kinase pathways in neuroblastoma sk-n-sh cells over expressing wild type human amyloid precursor protein 695,Neuroscience, 2007, pp. 386-395, vol. 150, Elsevier.

Qiu Xin, Chen Guo Hua, Wang Tao, Effects of Huanglian Jiedu Decoction on Free Radicals Metabolism and Pathomorphism of the Hippocampus in APP/PS1 Double Transgenic Mice, China Academic Journal Electronic Publishing House, Oct. 2011, pp. 1379-1382, vol. 31 No. 10, Natural Science Foundation of Hubei Province, China.

Xin Qiu, Guohua Chen, Gui Mei, Yuegu Wang, Kaixin Wang, Tao Wang, Pei Feng,Cerebroprotective efect of Huanglian Jiedu decoction on amyloid protein precursor/presenilin—1 double transgenic mice, Neural Regeneration Research, Mar. 2011, pp. 645-650, vol. 6 issue 9, Natural Science Foundation of Hubei Province, China.

Qian Kun Quan, Jue Wang, Xi Li, Yi Wang, Ginsenoside Rg1 Decreases Aβ1-42 Level by Upregulating PPARγ and IDE Expression in the Hippocampus of a Rat Model of Alzheimer's Disease, PLOS ONE, Mar. 2013, pp. 1-8, vol. 8 issue 3, PLOS ONE.

Edward Rockenstein, Magdalena Torrance, Anthony Adame, Michael Mante, Pazit Bar-On, John B. Rose, Leslie Crew and Eliezer Masliah, Neuroprotective Effects of Regulators of the Glycogen Synthase Kinase-3β Signaling Pathway in a transgenic Model of Alzheimer's Disease are Associated with Reduced Amyloid Precur-

(56) References Cited

OTHER PUBLICATIONS sor Protein Phosphorylation, Neurobiology of Disease, pp. 1981-1991, Feb. 21, 2007, vol. 27 No. 8, Society for Neuroscience, USA.
Nobuyasu Sekiya, Mosaburo Kainuma, Hiroaki Hikiami, Takako Nakagawa, Kazufumi Kouta, Yutaka Shimada and Katsutoshi Terasawa, Oren-gedoku-to and Keishi-bukuryo-gan-ryo Inhibit the Progression of Atherosclerosis in Diet-Induced Hypercholesterolemic Rabbits, Biol. Pharm. Bull., Feb. 2005, pp. 294-298, vol. 28 No. 2,Pharmaceutical Society of Japan, Japan.
Gopal Thinakaran, David B. Teplow, Robert Siman, Barry Greenberg, and Sangram S. Sisodia, Metabolism of the "Swedish" Amyloid Precursor Protein Variant in Neuro2a (N2a) Cells Evidence That Cleavage at the "b-Secretase" Site Occurs in the Golgi Apparatus*, The Journal of Biological Chemistry, Feb. 8, 1996, pp. 9390-9397, vol. 271, No. 16, The American Society for Biochemistry and Molecular Biology, Inc, USA.
T.H. Tsai, S.C. Liu, P.L. Tsai, L.K. Ho, A.Y.C. Shum& C.F. Chen, The effects of the cyclosporin A, a P-glycoprotein inhibitor, on the pharmacokinetics of baicalein in the rat: a microdialysis study, British Journal of Pharmacology, 2002, pp. 1314-1320, vol. 137 No. 8, Nature Publishing Group.
Gao-Xue Wang, Zhuang Zhou, Dong-Xin Jiang, Jing Han, Jian-Fu Wang, Liang-Wei Zhao, Jun Li, In vivo anthelmintic activity of five alkaloids from Macleaya microcarpa (Maxim) Fedde against Dactylogyrus intermedius in Carassius auratus, Veterinary Parasitology,2010, pp. 305-313, vol. 171,Elsevier.
Wang Shan, Jiang Ning, Zhou Wen Xia, Zhang Yong-Yiang, Effect of Huanglian' Jiedutang on expression of hippocampus proteomics in senescence accelerated mouse,China Journal of Chinese Materia Medica, Nov. 2007, pp. 2294-2297, vol. 32 No. 21.
Lei Wang, Shijun Yan, Wensheng Zhang,Effects of an early- and late-stage treatment with Geniposide on cognitive dysfunction n a transgenic mouse model relevant to Alzheimer's, International Conference on Molecular Neurodegeneration Shanghai, China Sep. 22-24, 2011, p. 1 vol. 7, Molecular Neurodegeneration.
Jinghua Xu, Yukihisa Murakami, Kinzo Matsumoto, Michihisa Tohda, Hiroshi Watanabe, Shaohui Zhang, Qinghai Yu, Jia Shen, Protective effect of Oren-gedoku-to (Huang-Lian-Jie-Du-Tang) against impairment of learning and memory induced by transient cerebral ischemia in mice, Journal of Ethnopharmacology, May 25, 2000, pp. 405-413, vol. 73,Elsevier Science Ireland Ltd.
Lingling Yang, Jianrong Hao, Jing Zhang, Wenjun Xia, Xifeng Dong, Xiaoyan Hu, Feng Kong and Xing Cui, Ginsenoside Rg3 promotes beta-amyloid peptide degradation by enhancing gene expression of neprilysin, Journal of Pharmacy and Pharacology, 2009, pp. 375-380, vol. 61.

Yilu Ye, Chunyan Huang, Lili Jiang, Xiangdi Shen, Shanyong Zhu, Yan Rao, Jue Wang & Qi Zhang, Huanglian-Jie-Du-Tang Extract Protects against Chronic Brain Injury after Focal Cerebral Ischemia via Hypoxia-Inducible-Factor-1α—Regulated Vasular Endothelial Growth Factor Signaling in Mice, Biol. Pharm. Bull, Dec. 16, 2011, pp. 355-361, vol. 35 No. 3, The Pharmaceutical Society of Japan, Japan.
Crtstak D. Hayes, Debleena Dey, Juan Pablo Palavicini, Hongjie Wang, Wataru Araki, Madepalli K. Lakshmana, Chronic Cladribine Administration Increases Amyloid Beta Peptide Generation and Plaque Burden in Mice, PLOS ONE, Oct. 3, 2012, pp. 1-9, vol. 7 issue 10, PLOS ONE.
Evidence Reports of Kamp Treatment 2010; Task Force for Evidence Reports/Clinical Practice Guideline Special Committee for EBM, the Japan Society for Oriental Medicine; Cardiovascular Diseases.
Ali Khoodami, Meredith A. Wilkes and Thomas H. Roberts, Techniques for Analysis of Plant Phenolic Compounds, Molecules, Feb. 19, 2013, pp. 2328-2375, vol. 18, Deparnent of Plant and Food Sciences, University of Sydney, Sydney, NSW 2006, Australia.
Yoichi Kondo, Fumio Kondo, Masato Asanuma, Ken-Ichi Tanaka and Norio Ogawa, Protective Effect of Oren-gedoku-to Against Induction of Neuronal Death by Transient Cerebral Ischernia in the C57BL/6 Mouse, Neurochemical Research, 2000, pp. 205-209, vol. 25, No. 2, Plenum Publishing Corporation.
Frank M. Laferla, Kim N. Green and Salvatore Oddo, Intracellular amyloid-β in Alzheimer's disease, Nature Reviews, Jul. 2007, pp. 499-509, vol. 8, Nature Publishing Group.
Orly Lazarov, Gerardo A. Morfini, Edward B. Lee, Mohamed H. Farah, Anita Szodoral, Scott R. Deboer, Vassilis E. Koliatsos, Stefan Kins, Virginia M. -Y. Lee, Philip C. Wong, Donald L. Price, Scott T. Brady and Sangram S. Slsodia, Axonal Transport, Amyloid Precursor Protein, Kinesin-1. and the Processing Apparatus: Revisited, The Journal of Neuroscience Mar. 2, 2005, pp. 2386-2395 vol. 25 No. 9, Society for Neuroscience.
Ming Sum Lee, Shih Chu Kai, Cynthia A. Lemere, Weiming Xia, Huang Chun Tseng, Ying Zhou, Rachel Neve, Michael K. Ahlijanian, and Li-Huei Tsai, APP processing is regulated by cytoplasmic phosphorylation, The Journal of Cell Biology, Oct. 13, 2003; page(s), vol. 163 No. 1, The Rockefeller University Press.
P Lewczuk, H Kamrowski-Kruck, O Peters, Theuser, F Jessen, J Popp, K Burger, H Hampel, L Frolich, S Wolf, B Prinz, H Jahn, CH Luckhaus, R Perneczky, Hull, J Schroder, H Kessler, J Pantel, H-J Gertz, H-W Klafki, H Kolsch, U Reulbach, H Esselmann, JM Maler, M Bibl, J Kornhuber and J Wiltfang, Soluble amyloid precursor proteins in the cerebrospinal fluid as novel potential biomarkers of Alzheimer's disease: a multicenter study, Molecular Psychiatry, Jul. 29, 2008, pp. 138-145, vol. 15.
Office Action of CN 2014102652071 issued from the State Intellectual Property Office of the People's Republic of China of Feb. 14, 2016.

COMPOSITION COMPRISING *RHIZOMA COPTIDIS, CORTEX PHELLODENDRI* AND *FRUCTUS GARDENIAE* AND FOR TREATING NEURODEGENERATIVE DISEASES

CROSS-REFERENCE TO RELATED APPLICATIONS

This application claims the benefit of U.S. Provisional Patent Application 61/834,437 filed on Jun. 13, 2013 and 61/836,118 filed on Jun. 17, 2013, the disclosures of which are incorporated by reference herein.

FIELD OF INVENTION

This invention is in the field of pharmaceuticals, health supplements and chemical industries. In particular, this invention provides a herbal composition with significant potent therapeutic effects for treating neurodegenerative diseases that does not associate with any β-amyloid increasing effect exhibited by existing treatments.

BACKGROUND OF INVENTION

Extracellular senile plaques and phosphorylated tau-associated intraneuronal neurofibrillary tangles (NFTs) are the two classical microscopic pathologies of Alzheimer's disease (AD). Senile plaques comprise a dense core of amyloid-β (Aβ) that is surrounded by dystrophic neurites as seen in Selkoe D J (2004) Cell biology of protein misfolding: the examples of Alzheimer's and Parkinson's diseases. Nat Cell Biol 6: 1054-1061. Aβ is a 39-43 amino acid proteolytic product of a larger amyloid precursor protein (APP). APP is an integral membrane protein processed by the proteases α-secretase or β-secretase to produce α-C terminal fragment (CTF-α) or β-C terminal fragment (CTF-β), respectively. These fragments are subsequently cleaved by α-secretase to produce P3 or Aβ respectively, and a cytoplasmic tail dubbed APP-intracellular domain (AICD). APP proteolysis also releases soluble forms of APP (sAPPα- and sAPPβ-), and these soluble APPs may also now be considered biomarkers for AD (P Lewczuk et al., Soluble amyloid precursor proteins in the cerebrospinal fluid as novel potential biomarkers of Alzheimer's disease: a multicenter study Mol Psychiatry. 2010; 15:138-45). On the other hand, monomeric Aβ (4.3 kDa molecular weight) self-assembles into oligomers (Selkoe D J (2004) Cell biology of protein misfolding: the examples of Alzheimer's and Parkinson's diseases. Nat Cell Biol 6: 1054-1061 and Hardy J, Selkoe D J (2002) The amyloid hypothesis of Alzheimer's disease: progress and problems on the road to therapeutics. Science 297: 353-356). These oligomers eventually deposit as large fibrils in extracellular space, which assemble as amyloid plaques. Although the precise mechanisms by which Aβ may induce neurotoxicity are still unknown. Several studies have proposed these mechanisms include calcium influx, generation of reactive oxygen species (ROS), nitric oxide (NO) production and increased phosphorylation of tau.

The US Food and Drug Administration has approved five drugs (i.e., tacrine, donepezil, rivastigmine, galantamine and memantine) for the treatment of AD (Lleó A, Greenberg S M, Growdon J H (2006) Current pharmacotherapy for Alzheimer's disease. Ann Rev Med 57: 513-533), but they produce only mild, symptomatic relief and do not halt progression of dementia. Therefore there is a need for alternative drugs for the treatment of AD. One source of phytotherapeutic agents is Huang-Lian-Jie-Du-Tang (HLJDT), a traditional Chinese medicine (TCM) achieving popularity for its therapeutic application.

HLJDT is a famous TCM formula widely used in treating stroke and dementia. It is composed of four herbs, namely: *Rhizoma coptidis* (RC) (*Coptis chinensis* Franch, or Huang Lian in Chinese), *Radix scutellariae* (RS) (*Scutellaria baicalensis* Georgi, or Huang Qin in Chinese), *Cortex phellodendri* (CP) (*Phellodendron amurense*, or Huang Bai in Chinese) and *Fructus gardeniae* (FG) (*Gardenia jasminoides* Ellis, or Zhi Zi in Chinese), in a 3:2:2:3 dry weight ratio. As stated in the traditional Chinese medicinal book Wai-Tai-Mi-Yao, RC, RS, and CP are major ingredients of HLJDT, and FG functions as an adjuvant constituent to support the effect of the principal ingredients. All traditional Chinese literatures so far document that HLJDT formula must consist all four herbs.

HLJDT has been used to treat senile dementia, inflammation, digestive system upsets, and cerebrovascular disease in China (Chen G H, Shan P, Qiu X (2007) The clinical study on Huanglianjiedu decoction on for patients with senile dementia, the type of hyperactivity of heart-fire and liver fire in TCM. Zhongguo Zhongyi Jizheng 16: 386-387). HLJDT has been used to treat various clinical symptoms linked with stroke and with vascular dementia in Japan (Otomo E, Togi H, Kogure K (1991) Clinical usefulness of TSUMURA Orengedokuto for the treatment of cerebrovascular disease: a well-controlled study comparing TSUMURA Orengedokuto versus Ca hopantenate, using sealed envelopes for allocation. Geriatric Medicine 29: 121-151 and Ito E, Takahashi A, Kazuya F (1991) Clinical effectiveness of TSUMURA Orengedokuto in the treatment of cerebral infarction. Geriatric Medicine 29: 303-313). In a Japanese clinical study, Okamoto H et al., (2013) Orengedoku-to augmentation in cases showing partial response to yokukan-san treatment: a case report and literature review of the evidence for use of these Kampo herbal formulae. Neuropsychiatr Dis Treat. 2013; 9:151-155, the addition of HLJDT to yokukan-san (Japanese traditional herbal medicine) exerted the same efficacy as aripiprazole (antipsychotics) in controlling aggressiveness in an Alzheimer's type dementia patient without any adverse effects.

Preclinical reports in Kondo Y, Kondo F, Asanuma M, Tanaka K, Ogawa N (2000) Protective effect of oren-gedoku-to against induction of neuronal death by transient cerebral ischemia in the C57BL/6 mouse. Neurochem Res 25: 205-209, Wang S, Jiang N, Zhou W X, Zhang Y Y (2007) Effect of Huanglian Jiedutang on expression of hippocampus proteomics in senescence accelerated mouse. Zhongguo Zhong Yao Za Zhi 32: 2289-2294, and Qiu X, Chen G H, Wang T (2011) Effects of huanglian jiedu decoction on free radicals metabolism and pathomorphism of the hippocampus in App/PS1 double transgenic mice. Zhongguo Zhong Xi Yi Jie He Za Zhi 31: 1379-1382 provide evidence that HLJDT can improve cerebral blood flow; it potently inhibits lipid peroxidation in the brain and thus preserves energy metabolism in the brain. Both ethanolic extracts and aqueous extracts of HLJDT can ameliorate the cognitive impairments induced by cerebral ischemia and central cholinergic dysfunction in animal models. Recently, Durairajan S S K, Liu L F, Lu J H, Chen L L, Yuan Q, Chung S K, Huang L, Li X S, Huang J D, Li M (2012) Berberine ameliorates β-amyloid pathology, gliosis, and cognitive impairment in an Alzheimer's disease transgenic mouse model. Neurobiol Aging 33: 2903-2919 shows that berberine, a compound in HLJDT, can significantly reduce the Aβ load in a transgenic Alzheimer's disease model by regulating APP processing. However, the exact mechanism underlying HLJDT-mediated cognitive improvements is not known. In the context of AD, there is a study of HLJDT in AD mice by Qiu X, Chen G H, Mei G, Wang Y G. (2011) Effects of huanglian jiedu decoction on free radicals metabolism and pathomorphism of the hippocampus in App/PS1 double transgenic mice Zhongguo Zhong Xi Yi Jie He Za Zhi 31: 1379-1382. Qiu et al. reported that HLJDT reduced Aβ plaques and improved memory in APP/PS-1 mice, but the authors did not mention the quantification of Aβ load. Qiu et al. also reported that HLJDT reduced APP mRNA level but did not measure the effect of HLJDT on the protein level of full length (F1)-APP, Aβ and soluble forms of APP, namely, sAPPα and sAPPβ.

Citation or identification of any reference in this section or any other section of this application shall not be construed as an admission that such reference is available as prior art for the present application.

SUMMARY OF INVENTION

An objective of this invention is to provide a herbal composition which improves the regulatory processing of amyloid-β protein precursor (APP), and that associates with a significant potent treatment for neural degenerative diseases and does not associate with any β-amyloid increasing effect exhibited by existing treatment. In particular, existing treatment HLJDT is shown to exhibit β-amyloid increasing effect.

In accordance with one aspect of the present invention, there is provided a composition (hereinafter refers to modified formula of HLJDT (HLJDT-M)) comprising *Rhizoma coptidis* (*Coptis chinensis* Franch, Huang Lian in Chinese), *Cortex phellodendri* (*Phellodendron amurense*, Huang Bai in Chinese) and *Fructus gardeniae* (*Gardenia jasminoides* Ellis, Zhi Zi in Chinese), in a dry weight ratio of 4:2:4 but excluding *Radix scutellariae* (*Scutellaria baicalensis* Georgi, Huang Qin in Chinese), for use in the treatment of neurodegenerative diseases.

In accordance with another aspect of the present invention, there is provided a composition consisting essentially of *Rhizoma coptidis*, *Cortex phellodendri* and *Fructus gardeniae*, in a dry weight ratio of 4:2:4 for use in the treatment of neurodegenerative diseases.

In accordance with another aspect of the present invention, that the composition excludes the active compound, baicalein for use in the treatment of neural degenerative diseases.

In accordance with a further aspect of the present invention, there is provided a method for prevention or treatment of neural diseases comprising administering to a mammal a composition comprising *Rhizoma coptidis* (Hunag Lian), *Cortex phellodendri* (Huang Bai) and *Fructus gardenia* (Zhi Zi), wherein the composition excludes *Radix scutellariae* (Huang Qin).

In accordance with a further aspect of the present invention, there is provided a method for prevention or treatment of neural diseases comprising administering to a mammal a composition consisting essentially of *Rhizoma coptidis*, *Cortex phellodendri* and *Fructus gardenia* in a dry weight ratio of (3.5-4.5):(1.5-2.5):(3.5-4.5); (3.8-4.2):(1.8-2.2):(3.8-4.2) or 4:2:4.

In accordance with a first embodiment of the present invention, the dry weight ratio of *Rhizoma coptidis* (Hunag Lian), *Cortex phellodendri* (Huang Bai) and *Fructus gardenia* (Zhi Zi) in the composition is (3.5-4.5):(1.5-2.5):(3.5-4.5); (3.8-4.2):(1.8-2.2):(3.8-4.2) or 4:2:4. In another embodiment, said composition is administered at least 25 mg/kg/day orally. In yet another embodiment, the composition is administered at 25-35, 27-32 or 29-31 mg/kg/day orally for at least 3 months. The composition may be administered for 4, 5, 6, 7, 8, 10, 11 or 12 months.

In accordance with a second embodiment of the present invention, wherein *Rhizoma coptidis*, *Cortex phellodendrii* and *Fructus gardenia* comprises herb, extract and active ingredient thereof or a combination thereof, but not *Radix scutellariae*.

In accordance with a third embodiment of the present invention, the composition further comprises at least one protoberberine alkaloid and at least one iridoid glycoside. Preferably, said at least protoberberine alkaloid comprises berberine, palmatine, berberrubine phellodendrine, columbamine, coptisine, epiberberine, jatrorrhizine, or a combination thereof; said iridoid glycoside is geniposie.

In accordance with a fourth embodiment of the present invention, said composition comprises an extract of *Rhizoma coptidis*, *Cortex phellodendri* and *Fructus gardeniae* extracted with water or an ethyl alcohol-water mixture.

In accordance with a fifth embodiment of the present invention, the neural diseases to be treated or prevented by the composition of the present invention comprise neural degenerative diseases.

In accordance with a sixth embodiment of the present invention, the neural diseases are diseases associated with abnormal protein aggregation or deposit in the nervous system, wherein the abnormal protein aggregation or deposit comprises generation and accumulation of amyloid-β peptide (Aβ), tau hyperphosphorylation and/or gliosis.

In accordance with an eighth embodiment of the present invention, the amyloid-β peptide generation is diminished by inhibiting the generation of soluble APPs, C-terminal fragments of APP or phosphorylation of APP through administering the composition of the present invention to a mammalian subject in needs thereof.

In accordance with a ninth embodiment of the present invention, the neural degenerative diseases comprise Alzheimer's disease, taupathies, cerebreal amyloid angiopathy, dementia, neural mood disorders, bipolar disorder, schizophrenia, depression, Tourette syndrome, ADHD and associated neuropsychiatric conditions.

In accordance with a tenth embodiment of the present invention, the mammal is human.

In accordance with an eleventh embodiment of the present invention, there is provided a method of preparing a composition for preventing or treating neurodegenerative diseases comprising:

grinding *Rhizoma coptidis*, *Cortex phellodendrii*, *Fructus gardenia* into powder form, passing the powder form of *Rhizoma coptidis*, *Cortex phellodendrii* and *Fructus gardenia* individually through filtration screen for at least thrice followed by ultrasonication in ethanol or ethyl alcohol-water mixture to obtain extracts of *Rhizoma coptidis*, *Cortex phellodendrii* and *Fructus gardenia*, combining the extracts of *Rhizoma coptidis*, *Cortex phellodendrii* and *Fructus gardenia*, removing the ethanol in the extracts, and freeze drying the extracts to form the composition. In one embodiment, the dry weight ratio of *Rhizoma coptidis*, *Cortex phellodendrii* and *Fructus gardenia* is (3.5-4.5):(1.5-2.5):(3.5-4.5); (3.8-4.2):(1.8-2.2):(3.8-4.2) or 4:2:4.

Those skilled in the art will appreciate that the invention described herein is susceptible to variations and modifications other than those specifically described.

This invention includes all such variation and modifications. This invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout this specification and the appended claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of this invention and apply throughout. Unless otherwise defined, all other technical terms used herein have the same meaning as commonly understood to one of ordinary skill in the art to which this invention belongs.

Other aspects and advantages of this invention will be apparent to those skilled in the art from a review of the ensuing description.

BRIEF DESCRIPTION OF DRAWINGS

The above and other objects and features of the present invention will become apparent from the following description of this invention, when taken in conjunction with the accompanying drawings, in which.

DETAILED DESCRIPTION OF INVENTION

Figure 1A:
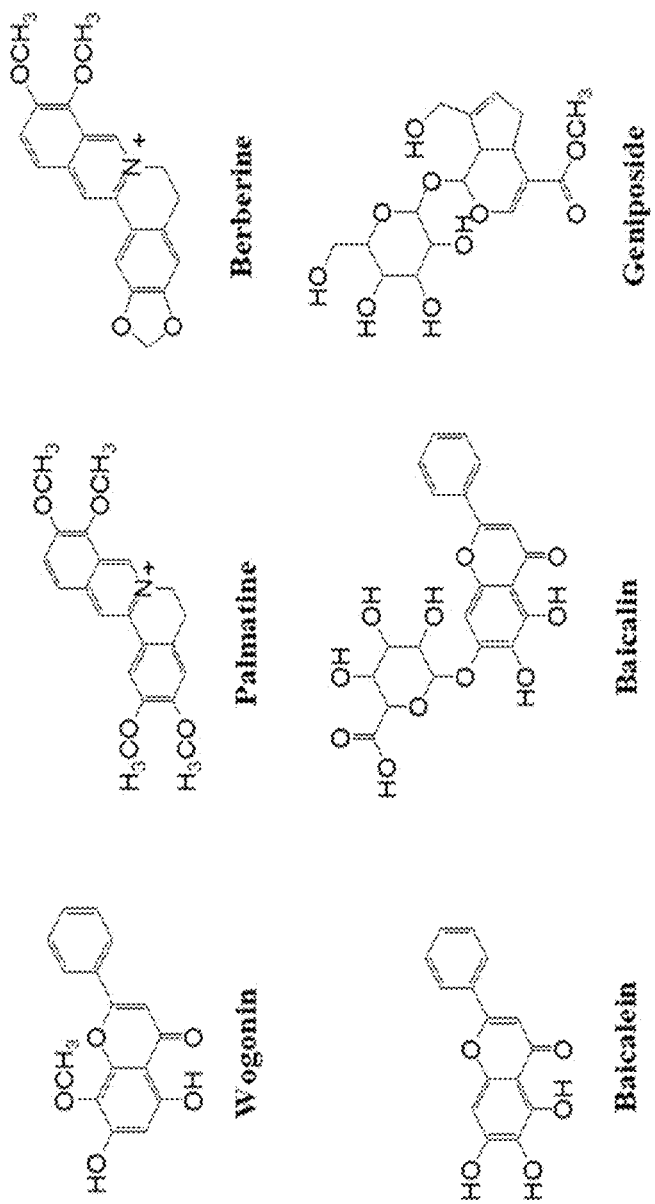
FIG. 1 shows chemical structures of active compounds found in the presently claimed composition, the modified formula of Huang-Liang-Jie-Du-Tang (HLJDT) (FIG. 1A); and qualitative analysis of: the modified HLJDT formula (at 245 nm) (A); *Fructus gardeniae* (FG) (at 245 nm) (B); *Rhizoma coptidis* (RC) (at 275 nm) (C); *Radix scutellariae* (RS) (at 275 nm) (D); *Cortex phellodendri* (CP) (at 275 nm) (E) (FIG. 1B). Peaks no. 1-6 represent: 1. Geniposide; 2. Berberine; 3. Palmatine; 4. Baicalein; 5. Baicalin; 6. Wogonin.

The present invention is not to be limited in scope by any of the specific embodiments described herein. The following embodiments are presented for exemplification only.

It is an objective of the present invention to provide an improved therapy in treating neurodegenerative diseases by reducing Aβ plaques and thereby improving the memory of patients. The inventors of the present invention find that the conventional HLJDT induces elevation of F1-APP, sAPPα, sAPPβ and intracellular Aβ (β-amyloid increasing effect) which reduces the therapeutic efficacy. The present invention does not induce elevation of F1-APP, sAPPα, sAPPβ and intracellular Aβ as compared to the conventional HLJDT. The present invention which excludes RS also shows potent therapeutic effect on treating neurodegenerative diseases. It is discovered by the present application that RS enhances Aβ (amyloid β-peptide) generation by increasing the protein level of APP which in turns reduces the efficacy of the conventional HLJDT in dementia therapy. The effects of the conventional HLJDT formula and the presently claimed composition which excludes RS on the APP processing and the generation of intracellular Aβ in an in vitro model (e.g., murine N2a cells stably expressing Swedish APP) are compared. The present application has meticulously evaluated each individual herbal component of HJLDT on the levels of different neurodegenerative disease markers, e.g. APP, sAPPα and sAPPβ, in order to formulate the composition of the present invention that associates with improved efficacy in treating neural degenerative diseases.

Material and Methods

Chemical and Reagents

Dulbecco's modified Eagle's medium (DMEM), fetal bovine serum (FBS), penicillin, streptomycin and G418 for cell culture were bought from Invitrogen (Carlsbad, Calif., USA).

Polyvinylidene Fluoride (PVDF) membrane was obtained from Hybond-P, GE Healthcare BioSciences (Piscataway, N.J., USA). Enhanced chemiluminescence (ECL) reagent was purchased from Thermo Scientific (Rockford, Ill., USA). Tetramethylbenzidine (TMB) was purchased from BD Biosciences (Sparks, Md., USA), while analytical grade reagents (including ethanol and methanol) were from Sigma-Aldrich (St. Louis, Mo., USA) unless otherwise indicated. Berberine, baicalin and baicalein were purchased from Sigma-Aldrich. Palmatine and geniposide were purchased from Aktin Chemicals (Chengdu, China).

Monoclonal 3-actin antibody was purchased from Santa Cruz Biotechnology (Santa Cruz, Calif., USA). Rabbit polyclonal CT15 antibody against the C-terminus of APP was a gift from Prof Edward Koo (University of California, San Diego, La Jolla, Calif., USA). Amino-terminus anti-Aβ1-17 monoclonal antibody (6E10) and a biotinylated Aβ17-24 (4G8) monoclonal antibody were ordered from Covance (Princeton, N.J., USA). Human anti-sAPPβ Swedish (sAPPβ-sw) monoclonal antibody (clone 6A1) was provided by IBL (Japan). Anti-pAPPThr668 polyclonal antibody was from Cell Signaling (Danvers, Mass., USA). Carboxy-terminus biotinylated anti-amyloid bG4(1-40)-5C3 (specific to a peptide corresponding to Aβ40) and bA4(1-42)-8G7 (specific to a peptide corresponding to Aβ42) antibodies were purchased from Nanotools (Teningen, Germany). The streptavidin-conjugated horseradish peroxidase (HRP) was purchased from DAKO (Carpinteria, Calif., USA). Aβ40 and Aβ42 peptides were provided by Invitrogen (Carlsbad, Calif., USA) and California Peptide (Napa, Calif., USA), respectively.

Plant Extraction

RC, RS, CP and FG are purchased from the Hong Kong Baptist University Mr. & Mrs. Chan Hon Yin Chinese Medicine Specialty Clinic and Good Clinical Practice Centre and from a local Chinese medicine pharmacy. All herbs were identified and authenticated by Prof. Zhong-Zhen Zhao from the School of Chinese Medicine, Hong Kong Baptist University, Hong Kong. Dry materials of the plants were ground into powder. Approximately 10 g of powder of each herbal component, and of the HLJDT (RC, RS, CP and FG in dry weight ratio of 3:2:2:3) and the present herbal composition (RC, CP and FG in a dry weight ratio of 4:2:4), are soaked in 100 mL of 80% ethanol for 1 hour, with sonication at a frequency of 120 kHz (SANHO Ultrasonic Engineering Ltd., Hong Kong); then extracted solutions are filtered. This procedure is repeated three times. This solvent is employed to standardize the extraction and to focus on screening. Approximately 300 mL of each extracted solution was collected and, then concentrated by rotary evaporation (EYELA, Tokyo Rikakikai Co., Ltd., Japan) under vacuum in a 60° C. water bath. All the extracts were finally subjected to lyophilization (LABCONCO, Laboratory Construction Company, MO, USA) at −40° C. under vacuum of 105 μbar. Each yield of plants was powdered and mixed until uniform, and then stored at 4° C. for later use. Dimethyl sulfoxide (DMSO) was used as the solvent to dissolve the extract, and it was loaded as the vehicle control for all cell cultures. Although the aqueous extract of HLJDT has been used in some studies, it was found that the ethanol extract was ideal to isolate most of the bioactive compounds with higher quantity from HLJDT when compared to aqueous extract. It was reported in Wang G X, Zhou Z, Jiang D X, Han J, Wang J F, Zhao L W, Li J. (2010). In vivo anthelmintic activity of five alkaloids from *Macleaya microcarpa* (Maxim) Fedde. Against *Dactylogyrus intermedius* in *Carassius auratus*. Vet Parasitol 171: 305-313 and Khoddami A, Wilkes M A, Roberts T H. (2013). Techniques for analysis of plant phenolic compounds. Molecules 18: 2328-2375 that ethanol can extract higher concentrations of flavonoid, polyphenols and more alkaloid compounds as compared to aqueous extract. Thus, ethanol is used in the present invention to standardize the extraction and to focus on screening. However, it is appreciated that aqueous extracts and aqueous-ethyl alcohol extracts of herbal components is also applicable in the present invention.

Chromatographic Conditions

Figure 1B:
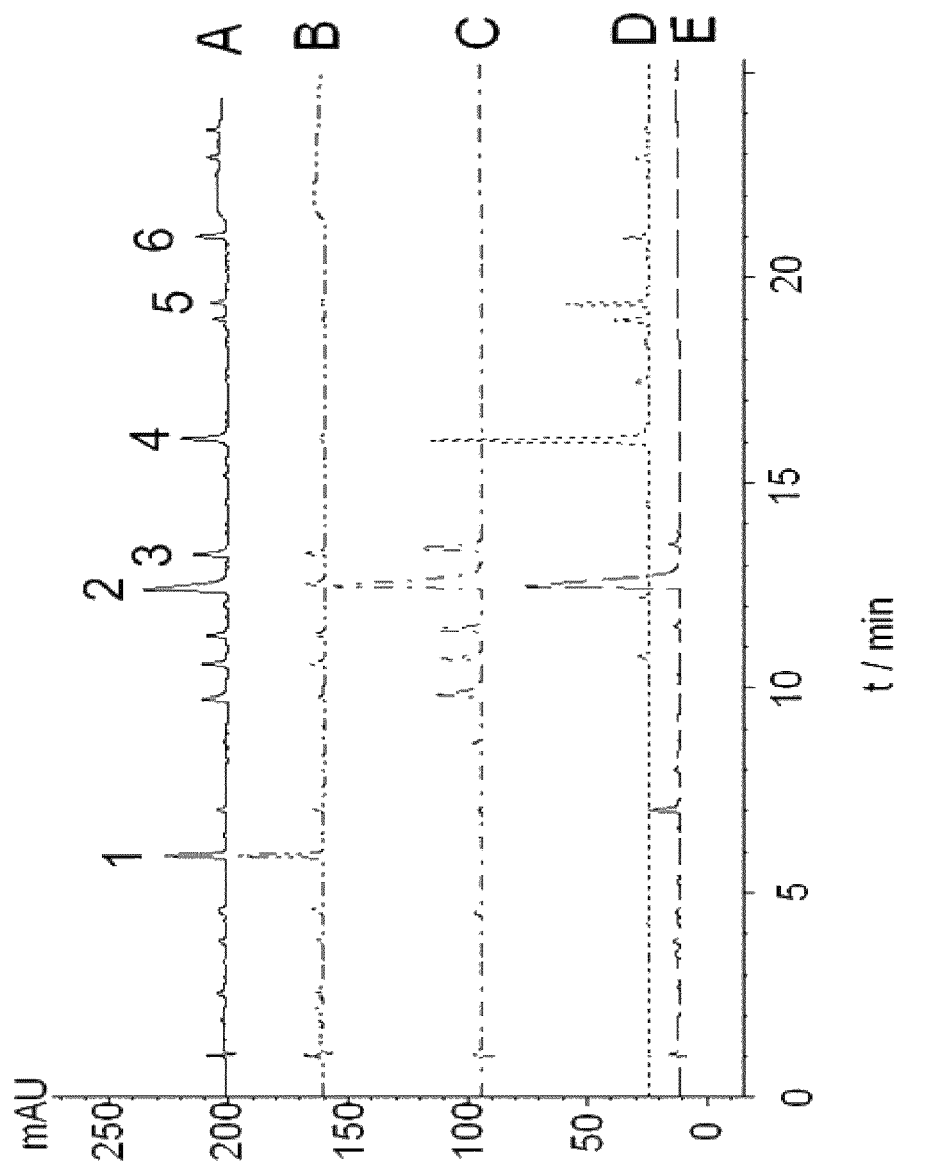

HPLC was carried out on an Agilent 1100 series with a G1315A diode array detector (California, USA). An Alltima™ C18 column (250×4.60 mm, particle size 5 μm) was used for separations. HPLC conditions were as follows: eluent A, 0.1% formic acid in H2O; eluent B, methanol with a linear gradient elution (0 min, 15% B; 0~15 min, 15%→38% B; 15~30 min, 38%→90% B; 30~30.1 min, 90%→100% B; 30.1~33 min, 100% B; 33~33.1 min, 100%→15% B; 33.1~36 min, 15% B) at a flow of 1 mL/min. Peaks were assigned by matching their retention times with that of each reference compound eluted in parallel with the same mobile phase. The concentrations of the analytes were determined from representative calibration curves (Table 1). From the HPLC profiles of ethanolic extract of HLJDT and its individual herbs, it is found that, in comparing the concentrations of six known components (geniposide, berberine, palmatine, baicalein, baicalin and wogonin) that can be found in ethanolic extract, berberine is most abundant (6.02%), followed by geniposide (4.01%), baicalin (2.67%), baicalein (1.31%), palmatine (0.867%) and wogonin (0.615%) (FIG. 1B, Table 1). Based on the four herbal components of HLJDT, geniposide is contributed by FG; berberine and palmatine are mainly found in RC and CP, respectively; and baicalin, baicalein and wogonin are contributed by RS. Recent studies in Durairajan S S K, Liu L F, Lu J H, Chen L L, Yuan Q, Chung S K, Huang L, Li X S, Huang J D, Li M (2012) Berberine ameliorates β-amyloid pathology, gliosis, and cognitive impairment in an Alzheimer's disease transgenic mouse model. Neurobiol Aging 33: 2903-2919, Lu J H, Ardah M T, Durairajan S S K, Liu L F, Xie L X, Fong W F, Hasan M Y, Huang J D, El-Agnaf O M, Li M (2011) Baicalein inhibits formation of α-synuclein oligomers within living cells and prevents Aβ peptide fibrillation and oligomerisation. Chembiochem 12: 615-624, and Wang L, Yan S and Zhang W S (2012) Effects of an early- and late-stage treatment with Geniposide on cognitive dysfunction in a transgenic mouse model relevant to Alzheimer's disease. Mol Neurodegener 7: S4, have shown that berberine, baicalein and geniposide have neuroprotective effects in Alzheimer's disease models. Therefore, these three compounds (FIG. 1A) were used for quantitative analysis of ethanolic extract of HLJDT.

Table 1 shows the contents (%) of geniposide, berberine, palmatine, baicalin, baicalein and wogonin in each herbal extract of HLJDT quantified by HPLC analysis

| Components | Contents (%) | | | | |
|---|---|---|---|---|---|
| | RC | RS | CP | FG | HLJDT |
| Geniposide | / | / | / | 19.44 | 4.01 |
| Baicalin | / | 5.57 | / | / | 2.67 |
| Palmatine | 2.69 | / | 0.409 | / | 0.867 |
| Berberine | 14.9 | / | 19.49 | / | 6.02 |
| Baicalein | / | 1.62 | / | / | 1.31 |
| Wogonin | / | 0.948 | / | / | 0.615 |

Remarks: "/" refers to undetected

Figure 2A:
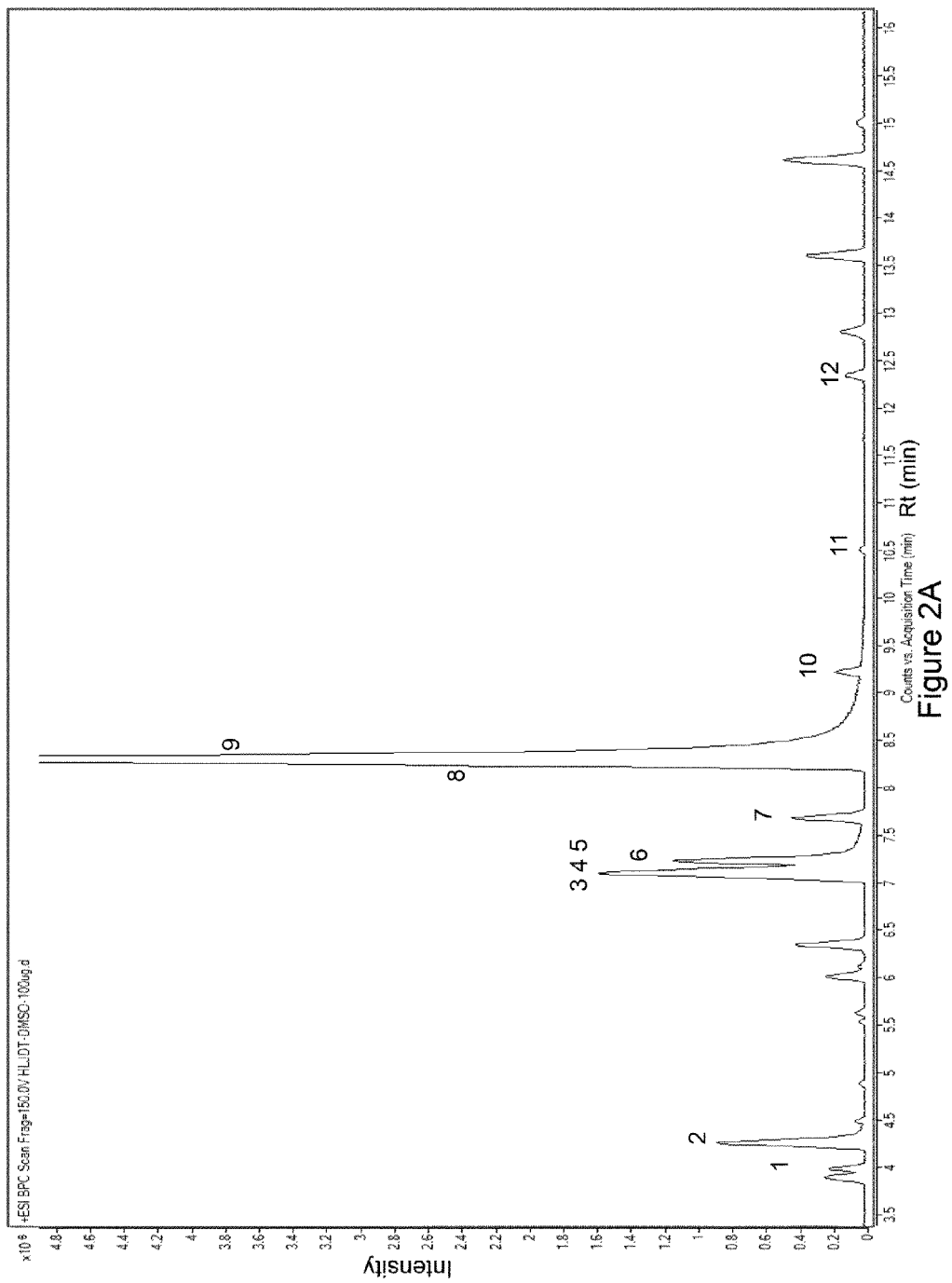
FIG. 2 shows ultra-high performance liquid chromatography with quadrupole time-of-flight mass spectrometry (UHPLC-Q-TOF-MS) typical base peak chromatogram (FIG. 2A) and extracted ion chromatograms (FIG. 2B) of the HLJDT extracts. 1. Geniposide; 2. Phellodendrine; 3. Columbamine; 4. Coptisine; 5. Epiberberine; 6. Jatrorrhizine; 7. Baicalin; 8. Palmatine; 9. Berberine; 10. Wogonoside; 11. Baicalein; and 12. Wogonin.
Figure 2B:
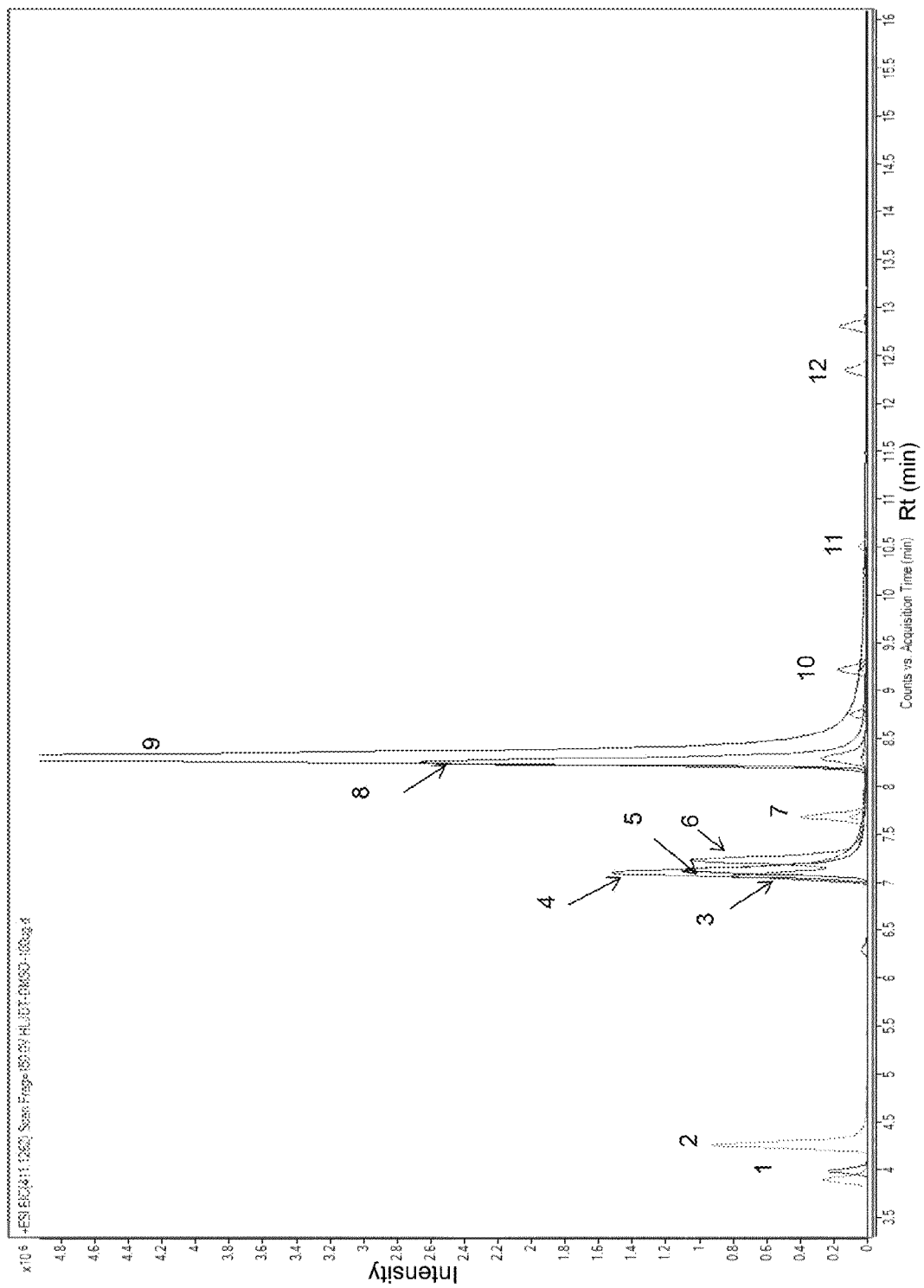
Figure 3A:
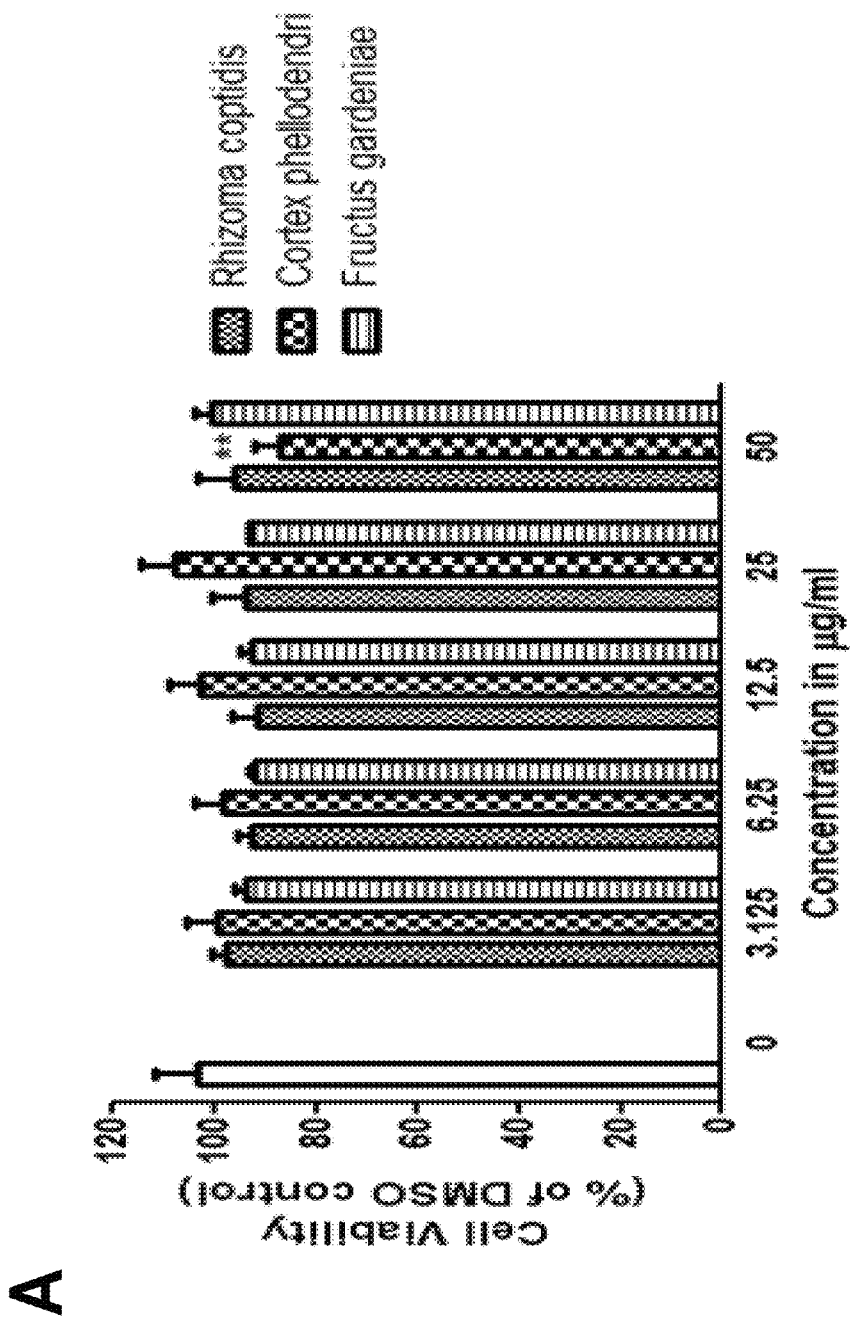
FIG. 3 shows the effects of HLJDT, HLJDT-M, constituent herbs and constituent compounds on toxicity in N2a-SwedAPP cells. N2a-SwedAPP cells were treated with the ethanolic extracts of RC, CP, FG (FIG. 3A), or RS (FIG. 3B); HLJDT or HLJDT-M (FIG. 3C); and berberine or baicalein (FIG. 3D). Cell viability was determined by MTT assay. The values denote the results of three experiments and are shown as mean±S.E.M.
Figure 3B:
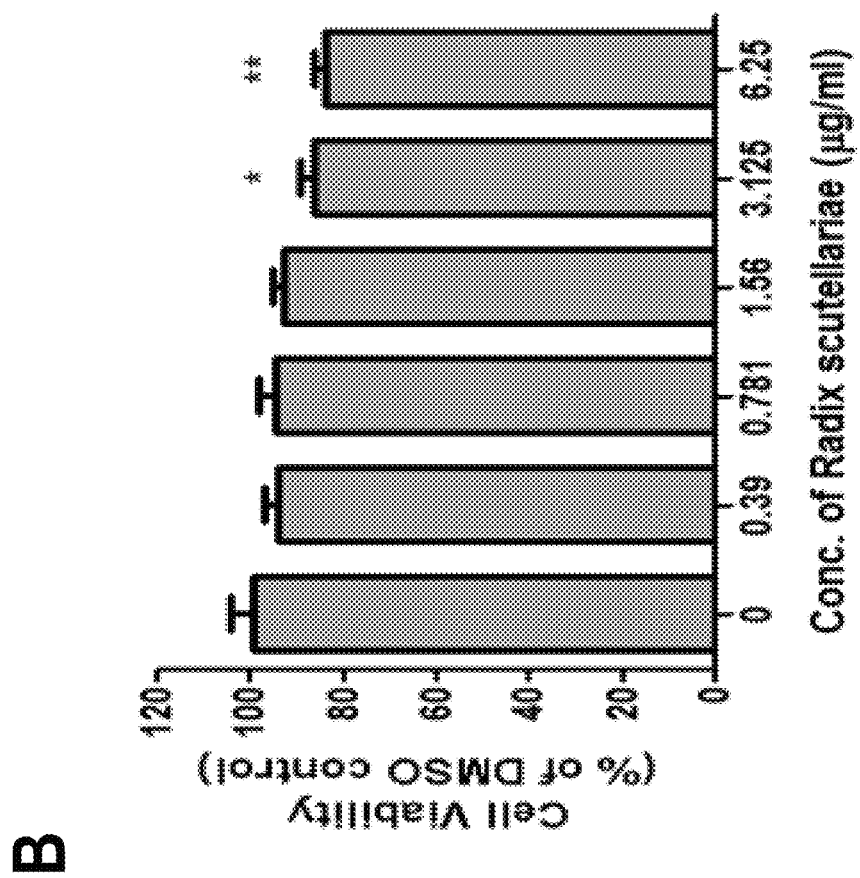
Figure 3C:
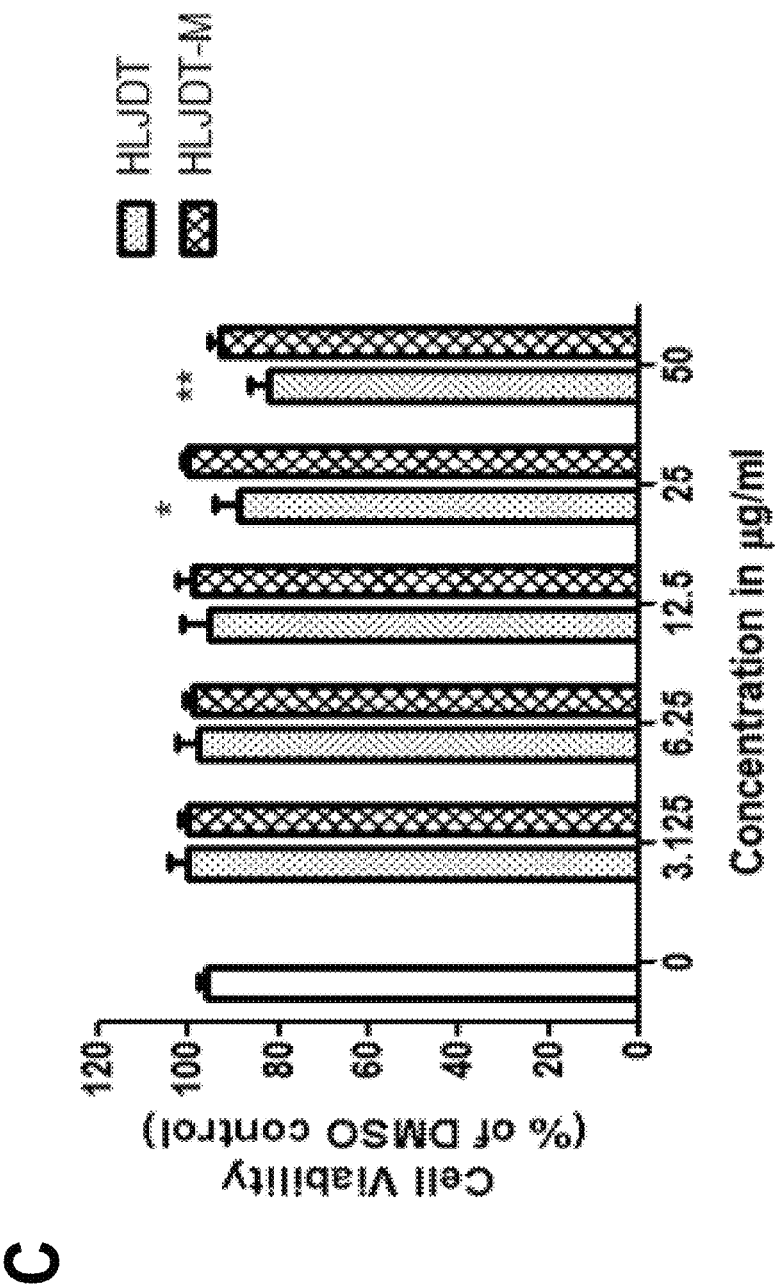
Figure 3D:
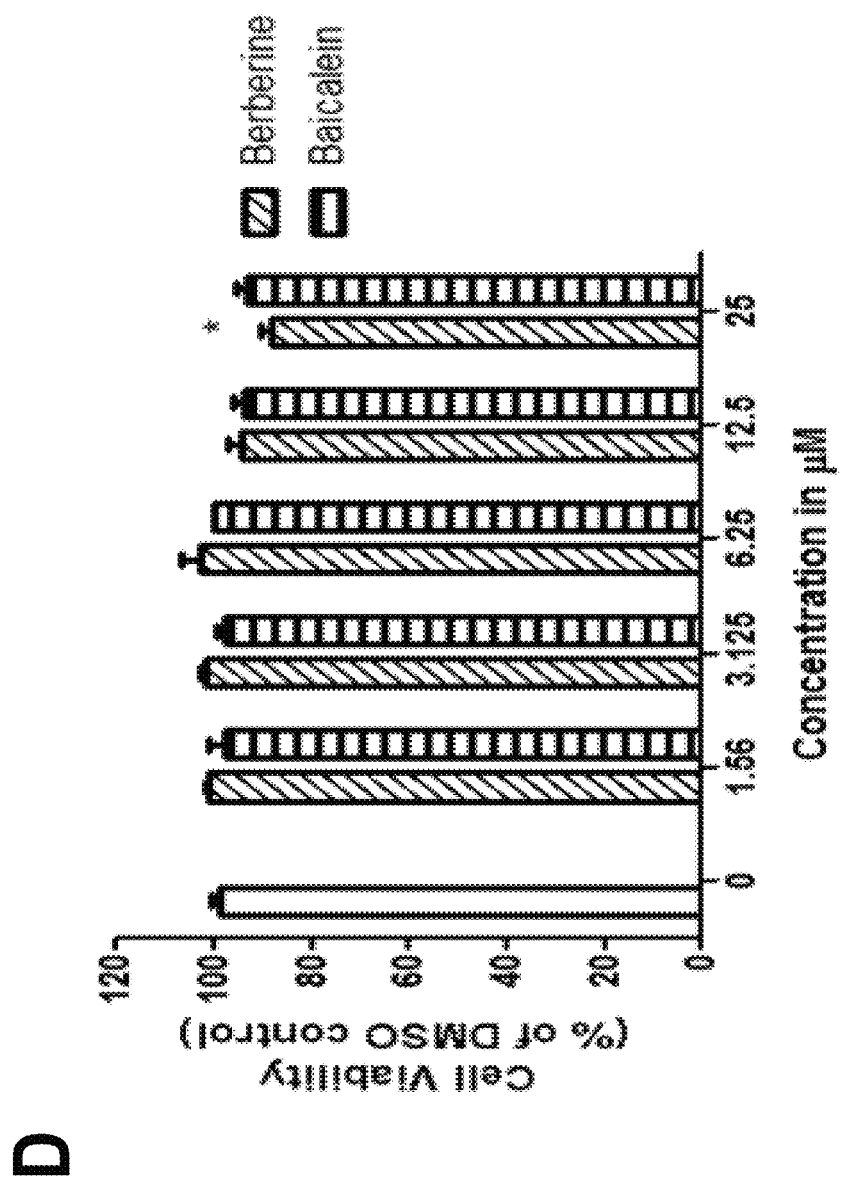

Qualitative identification of 12 active compounds of HLJDT was also performed by ultra-high performance liquid chromatography with quadrupole time-of-flight mass spectrometry (UHPLC-Q-TOF-MS) analysis with positive mode ESI-MS. A database was prepared for the identification of phytoconstituents of HLJDT based upon their molecular masses, calculated m/z values and retention times (Rt) observed in the analysis. Representative LC-MS base peak chromatograms (BPC) and extracted ion chromatograms (EIC) are shown in FIGS. 2A and 2B, respectively. By matching the Rt and m/z values between samples and reference standard solutions (Table 2), twelve characteristic peaks of HLJDT were identified in HLJDT sample solutions as geniposide, coptisine, jatrorrhizine, baicalin, palmatine, berberine, baicalein, wogonin, phellodendrine, columbamine, epiberberine and wogonoside were identified based on published articles related to the profiling of chemical components of HLJDT such as Chen J, Wang F, Liu J, Lee F S, Wang X, Yang H (2008) Analysis of alkaloids in *Coptis chinensis* Franch by accelerated solvent extraction combined with ultra performance liquid chromatographic analysis with photodiode array and tandem mass spectrometry detections. Anal Chim Acta. 613: 184-195, and Luo J L, Lu F L, LiuYC, Lo C F (2012) Identification of *Scutellaria Baicalensis* in Traditional Chinese Medicine Preparations by LC/MS/MS Fingerprinting Method. J Food Drug Anal 20: 887-899.

Table 2 shows the analytical condition of LC-MS for the identification of the 12 compounds detected in HLJDT by LC-MS

| Peak No. | Rt (min) | MS, m/z | Molecular formula | Identification |
|---|---|---|---|---|
| 1. | 3.99 | 411.1262 [M + Na]+ | $C_{17}H_{24}O_{10}$ | Geniposide |
| 2. | 4.29 | 342.1705 [M]+ | $C_{20}H_{24}NO_4$ | Phellodendrine |
| 3. | 7.05 | 338.1392[M]+ | $C_{20}H_{20}NO_4$ | Columbamine |
| 4. | 7.11 | 320.0917[M]+ | $C_{19}H_{14}NO_4$ | Coptisine |
| 5. | 7.13 | 336.1230[M]+ | $C_{20}H_{18}NO_4$ | Epiberberine |
| 6. | 7.23 | 338.1392[M]+ | $C_{20}H_{20}NO_4$ | Jatrorrhizine |
| 7. | 7.69 | 447.0922[M + H]+ | $C_{21}H_{18}O_{11}$ | Baicalin |
| 8. | 8.25 | 352.1543[M]+ | $C_{21}H_{22}NO_4$ | Palmatine |
| 9. | 8.29 | 336.1230[M]+ | $C_{20}H_{18}NO_4$ | Berberine |
| 10. | 9.21 | 461.1078[M + H]+ | $C_{22}H_{26}O_{11}$ | Wogonoside |
| 11. | 10.51 | 271.0601[M + H]+ | $C_{15}H_{10}O_5$ | Baicalein |
| 12. | 12.35 | 285.0757[M + H]+ | $C_{16}H_{12}O_5$ | Wogonin |

Cell Culture

N2a-SwedAPP cells were obtained from Dr. Gopal Thinakaran (University of Chicago, Chicago, Ill., USA). N2a-SwedAPP cells were cultured in Dulbecco's modified Eagle's medium (DMEM) and OPTI-MEM medium in a 1:1 ratio with 5% FBS, 50 µg/mL penicillin, 50 µg/mL streptomycin and 200 µg/mL G418 as previously described in Thinakaran G, Teplow D B, Siman R, Greenberg B, Sisodia S S (1996) Metabolism of the "Swedish" amyloid precursor protein variant in neuro2a (N2a) cells. J Biol Chem 271: 9390-9397. N2a-SwedAPP cells were incubated at 37° C. in a 5% CO2/95% humidity incubator. Cells were seeded 24 hours prior to the treatments. When growth reached close to 90% of confluence, cells were transferred into DMEM with 1% FBS for loading extracts. The final concentration of DMSO in all experiments was 0.1%, and this concentration caused no cytotoxicity.

Viability Assay

For the viability assay, N2a-SwedAPP cells were seeded in a 96-well plate (7000 cells/well and 5000 cells/well). The exhausted medium was replaced after 24 hours with 200 µL DMEM with 1% FBS and various concentrations (0, 3.125, 6.25, 12.5, 25 or 50 µg/mL) of each extract or various concentrations (0, 3.125, 6.25, 12.5 or 25 µM) of berberine or baicalein, and cells were incubated at 37° C. in 5% CO2 for 48 hours. Then the media were removed and 100 µL of phenol red-free DMEM containing 3-(4,5-dimethylthiazol-2-yl)-2, 5-diphenyltetrazolium bromide (MTT) was added to each well to a final concentration of 0.5 mg/mL and further incubated for 4 hours. The MTT-containing medium was removed, and the cell crystals were dissolved using 100 µL of 20% sodium dodecyl sulfate (SDS) in 50% N, N-dimethylformamide. Finally, optical intensity was measured using a BioRad plate reader at 570 nm and a reference of 620 nm. Experiments conducted independently three times.

Detection of Intracellular APP and Soluble APPs in N2a-SwedAPP Cells

To detect the levels of APP metabolic products, the cell lysates and the conditioned media were prepared as described in Durairajan S S K, Liu L F, Lu J H, Koo I, Maruyama K, Chung S K, Huang J D, Li M. (2011) Stimulation of non-amyloidogenic processing of amyloid-β protein precursor by cryptotanshinone involves activation and translocation of ADAM10 and PKC-α. J Alzheimer's Dis 25: 245-262, with minor modification. N2a-SwedAPP cells were seeded at a density of $4 \times 10^5$/mL in DMEM medium in a 6-well plate and cultured for 1 day. After transfer, cells were treated with different doses of RC, CP, FG and RS for 48 hours, then the extracellular media were collected for detection of sAPPα and sAPPβ-sw, and cells were harvested to quantify F1-APP and β-actin by Western blot analysis, as described previously by Durairajan et al. For intracellular APP, APP-CTFs and Aβ preparation, cells were washed with ice-cold PBS twice and solubilized in ice-cold RIPA buffer with protease inhibitor cocktail added. Lysates were collected and centrifuged at 16,000×g for 15 minutes at 4° C. The resulting supernatants were collected, and their protein concentrations were determined with bicinchoninic acid (BCA) protein assay reagent (Thermo Scientific, IL, USA). For sAPPα and sAPPβ-sw detection, the conditioned media are collected and frozen in liquid nitrogen, subjected to lyophilization at −40° C. under vacuum of 105 µbar for 2 days in order to remove all liquid. The conditioned media were standardized to total cell lysate protein.

Animals and Baicalein Treatment

All animal handling experiments were approved by the Hong Kong Baptist University Committee on the Use of Human and Animal Subjects in Teaching and Research (HASC, approval #: 12-13/0030). TgCRND8 mice expressing human APP with Swedish (K670N/M671L) and Indiana (V717F) mutations were used to evaluate the effect of baicalein on Aβ. Heterozygous TgCRND8 mice on a C57BL/6J background were used to breed a colony of experimental animals. The TgCRND8 mouse is an early onset model of AD with visible Aβ deposits in the brains of the animals starting from 3 months of age as described in Chishti M A, Yang D S, Janus C, Phinney A L, Home P, Pearson J, Strome R, Zuker N, Loukides J, French J, Turner S, Lozza G, Grilli M, Kunicki S, Morissette C, Paquette J, Gervais F, Bergeron C, Fraser P E, Carlson G A, George-Hyslop P S, Westaway D. (2001) Early-onset amyloid deposition and cognitive deficits in transgenic mice expressing a double mutant form of amyloid precursor protein 695. J Biol Chem 276: 21562-21570. The animals are housed in a controlled environment under a 12/12 hours light/dark cycle. They are allowed free access to food and water. The oral administration of baicalein (25 mg/kg/d) is commenced at 2 months of age and ended at 5 months before being killed. A single dose (25 mg/kg/d) of baicalein is tested in animal study as no difference in baicalein levels in the brain between doses of 25 and 50 mg/kg/d is found in our pilot study. Control mice orally gavaged with tap water only for the same administration period. At the conclusion of the treatment period, mice were deeply anesthetized by chloral hydrate and perfused with phosphate buffered saline (PBS). The brains were then dissected and processed for Aβ immunostaining Serial Differential Fractionation with Ultracentrifugation To detect differences in the level of APP metabolic products among treatment groups, the levels of Aβ, F1-APP, pAPPThr668, CTFs, sAPPα and sAPPβ-sw are measured after a 3-step sequential extraction using Tris buffered saline (TBS) (pH 7.4), 1% Triton X-100/TBS (TBSX) and formic acid (FA) methods as described in Youmans K L, Leung S, Zhang J, Maus E, Baysac K, Bu G, Vassar R, Yu C, LaDu M J. (2011) Amyloid-β42 alters apolipoprotein E solubility in brains of mice with five familial AD mutations. J Neurosci Methods 196: 51-59. All extraction buffers also contained protease and phosphatase inhibitor cocktail (Roche Diagnostics, Basel, Switzerland). Snap frozen tissue is homogenized in 15 volumes (w/v) of TBS homogenization buffer and centrifuged at 100,000×g for 1 h at 4° C. using a Type 70 Ti rotor in an Optima™ L-80XP Ultracentrifuge (Beckman Coulter, Fla., USA). The TBS-soluble fraction is aliquoted, frozen in liquid nitrogen and stored at −80° C. The pellets are resuspended in 15 volumes of TBSX and kept on ice for 30 minutes, followed by a second centrifugation at 100,000×g for 1 hour at 4° C. The TBSX soluble fraction is aliquoted, frozen and stored as for the TBS fraction. The TBSX-insoluble pellet is resuspended in 2 mL of 70% FA and centrifuged at 100,000×g at 4° C. for 1 hour. The FA extracts are neutralized by the addition of 20 volumes of 1 M Tris pH 11, aliquoted and stored at −80° C. Total protein content in TBS- and TBSX-extracts is determined via BCA assay. Total protein in FA-extracts is determined by Bradford Protein Microassay (Bio-Rad, CA, USA).

Aβ Measurements

The levels of intracellular Aβ1-40 and Aβ1-42 are quantified by using a sandwich ELISA as previously described by Durairajan et al., 2011 with minor modification. Equal amounts of cell or brain lysates are used for Aβ quantification by sandwich ELISA. The monoclonal antibody 6E10 is used as the capture antibody by adding to ELISA plates (0.2 μg diluted in 0.1 M Na2CO3 (pH 9.6) per well) and incubated overnight at 4° C. The plates are washed with PBS (0.05% Tween 20) and blocked with 4% BlockAce (Serotec, Raleigh, N.C., USA) for 2 hours at room temperature. Equilibrated protein lysates from each treatment (a 100 μL volume is adjusted in all treatment groups by using PBS) are applied in duplicate and incubated at room temperature for 2 hours with constant rotation at 30 rpm. Biotinylated monoclonal anti-Aβ40 5C3 (50 ng per well) and biotinylated monoclonal 8G7 (50 ng per well) antibodies are used for detection of Aβ1-40 and Aβ1-42, respectively, and are diluted in 1% BlockAce and incubated for 2 hours at room temperature. Plates are thoroughly washed with PBS (0.05% Tween 20), and streptavidin conjugated HRP is added for 1 hour at room temperature. Finally the plates are washed four times with PBST before adding the substrate TMB for 30 minutes. Absorbance at 450 nm is measured in duplicate wells after addition of 2 M H2SO4. All ELISA experimental data are from three different days. Synthetic Aβ40 and Aβ42 peptides are used for construction of calibration curves, and Aβ is measured in lysates.

SDS-PAGE and Western Blot Analysis

For Western blot analysis from cell culture or mouse brain, 10-30 μg total protein is separated on 10% and 15% SDS-PAGE gels and blotted onto PVDF membranes for the detection of full length APP (F1-APP), CTFs, sAPPα, sAPPβ-sw, 3-actin and phosphorylated APP (pAPPThr668). After blocking with 5% skimmed milk, the blots are incubated with primary antibodies overnight at 4° C. with shaking. Blots are washed and incubated with HRP-conjugated secondary antibodies. The goat anti-mouse IgG is used when the primary antibody is 6E10 (1:1000), sAPPβ-sw (1:100), or anti-β-actin (1:5000), and the goat anti-rabbit IgG is used when the primary antibody is anti-CT15 (1:5000) or pAPPThr668 (1:1000). After incubation with HRP-conjugated secondary antibody, immunoblots are treated with ECL and developed using X-ray films (Fujifilm). Films are scanned, and the band intensity is analyzed using Image J software (NIH Image).

Membranes probed with primary antibodies CT15 and 6E10 is stripped using stripping buffer (62.5 mM Tris-HCl pH 7.6, 100 mM 2-mercaptoethanol and 2% SDS) at 60° C. for 20 minutes, then washed with a generous amount of TBST for 20 mins twice and finally blocked with 5% milk for 1 hour. Stripped CT15 and 6E10 probed membranes are reincubated with pAPPThr668 and sAPPβ-sw 6A1 antibodies, respectively.

Immunohistochemistry

Immunohistochemistry and image analysis of Aβ plaques is performed on coronal brain sections from TgCRND8 mice treated with baicalein or tap water as described previously by Durairajan et al. 2012. For immunohistochemical analysis, 30 μm thick sections are obtained using a Thermo Shandon Cryotome™ (Thermo Sceintific) slicing system. The free-floating sections are quenched for the endogenous peroxidase activity, and the sections are incubated overnight at 4° C. with a biotinylated 4G8 antibody (1:1000). After removing excess primary antibody, sections are washed 3 times, and immunostaining is performed using a Vectastain ABC Elite kit (Vector Laboratories, Burlingame, Calif., USA) linked with the diaminobenzidine reaction. Images are obtained with a Nikon fluorescent inverted microscope with digital Nikon camera and analyzed by Image J software. Aβ plaque burden is calculated as the area occupied by the Aβ plaques as a percentage of total area of the brain sections.

Statistical Analysis

The results are displayed as mean±standard error (SE), with n=3 or 5 per group for all comparisons. Statistical analysis is performed by one-way analysis of variance (ANOVA) followed by Fisher's Least Significant Difference (LSD) for in vitro experiments. In animal experiments, the student T test is performed. Statistical significance is accepted at $*p<0.05$, $p<0.01$ and $*p<0.001$.

Results
Cell Viability
N2a-SwedishAPP cells are widely used as a cellular model of Alzheimer's disease, because they express a high level of APP and Aβ. The effects of HLJDT and its components on viability of N2SwedAPP cells are monitored by using the MTT assay. Extracts of individual herbal component, HLJDT components and the present invention (HLJDT-M) are ascertained for cytotoxicity for at least 48 hours at five different concentrations; the highest concentration that shows greater than 90% cell viability is considered as the non-toxic concentration (FIG. 3A-D). The DMSO concentration is 0.1% throughout the experiments and there is no cytotoxicity at this concentration. The non-toxic concentrations of RC (50 µg/mL), CP (25 µg/mL), FG (50 µg/mL), RS (1.56 µg/mL), HLJDT (12.5 µg/mL) HLJDT-M (25 µg/mL), berberine (12.5 µM) and baicalein (12.5 µM) are used to investigate the APP modulating effects on N2SwedAPP cells for 48 hours. According to the contents of pure compounds in each herbal component of HLJDT (Table 1), there is a correlation between the effective concentration of berberine in RC (11 µM of berberine in 25 µg/mL of RC) and berberine (12.5 µM) alone, however, there is no exact correspondence between the highest effective concentration of baicalein in RS (0.1 µM of baicalein in 1.56 µg/mL of RS) and baicaein (12.5 µM) alone. The non-toxic concentrations of HLJDT components are used in the following experiments.

Modulation of APP Processing by RC, RS, CP, and FG

Western blotting of N2a-SwedAPP cells is used to test differences in the processing of Swedish mutant APP by HLJDT components. Several antibodies are used in Western blot analysis: CT15 recognizes full length APP (F1-APP), 6E10 identifies only α-secretase-cleaved APP i.e sAPPα, and the sAPPβ-sw specific for β-secretase cleavage of Swedish mutant APP. Several studies suggest that APP phosphorylation affects the maturation and subcellular distribution of APP, increases production of CTFs, and stimulates generation of Aβ, therefore APP phosphorylated at threonine 668 using an antibody to pAPPThr688 is examined.

Figure 4A:
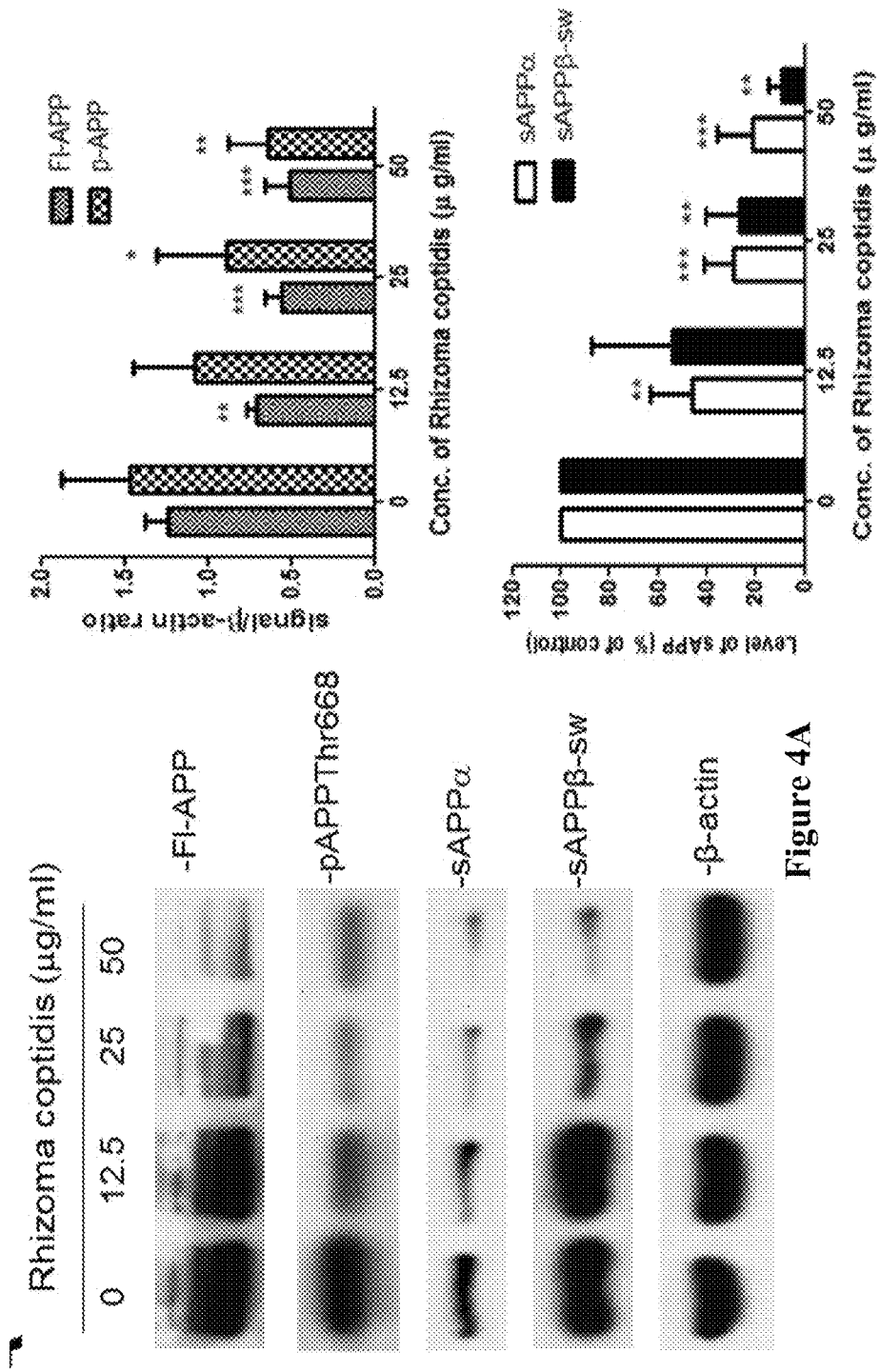
FIG. 4 shows the effects of herbal extracts of HLJDT in altering the processing of APP in N2a-SwedAPP cells. Conditioned medium and cell lysates are prepared from N2a-SwedAPP cells that were treated with RC (FIG. 4A), CP (FIG. 4B), FG (FIG. 4C) or RS (FIG. 4D) at various doses as indicated for 48 hours. Western blotting was used to detect sAPPα and sAPPβ-sw in conditioned medium, and to detect F1-APP, pAPPThr668 and β-actin in cell lysates. Bars represent mean±S.E.M. for three experiments.
Figure 4B:
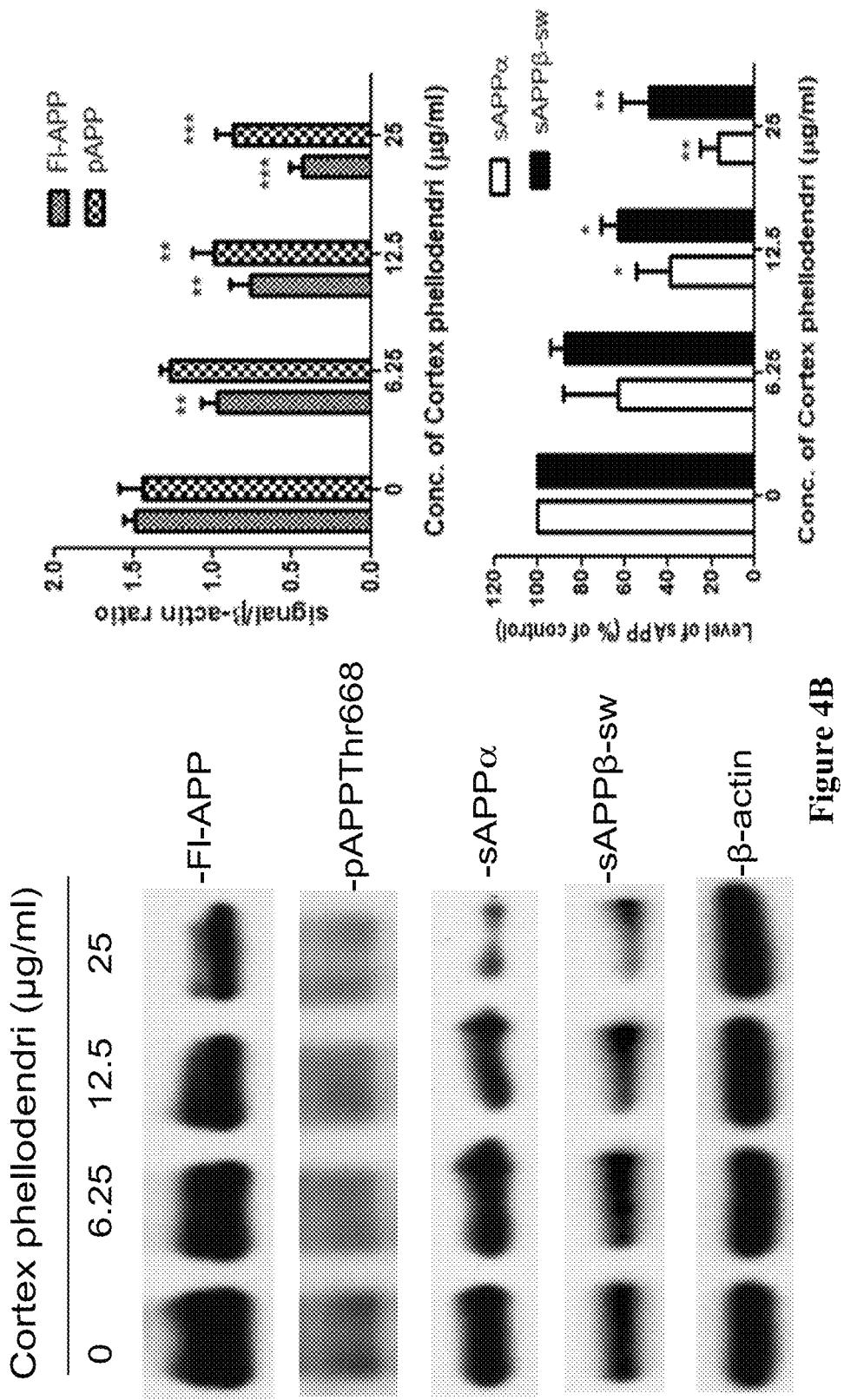

As shown in FIG. 4, the levels of F1-APP, pAPPThr688 and soluble APPs (sAPPα and sAPPβ-sw) are decreased by treatment with RC or CP in a concentration-dependent manner (FIGS. 4A and 4B). A low concentration of RC and CP (12.5 µg/mL) reduces the F1-APP level by 42% and 38%, respectively. At 25 µg/mL, F1-APP is reduced by 55% and 71% by RC and CP, respectively. Treatment with RC or CP decreases the level of phosphorylated APP. At 25 µg/mL, pAPPThr668 is reduced by 39.5% and 40.5% by RC and CP, respectively. Thus, both RC and CP can reduce the levels of F1-APP and pAPPThr668. There is also a significant decrease in the levels of sAPPα and sAPPβ-sw. The level of sAPPα is reduced by 71% ($p<0.001$) and 83% ($p<0.01$) by treatment with RC and CP, respectively, at a concentration of 25 µg/mL. Similarly, the level of sAPPβ-sw drops significantly upon treatment with 25 µg/mL ($p<0.01$) of RC or CP, but 12.5 µg/mL of RC has no significant effect ($p>0.05$).

Figure 4C:
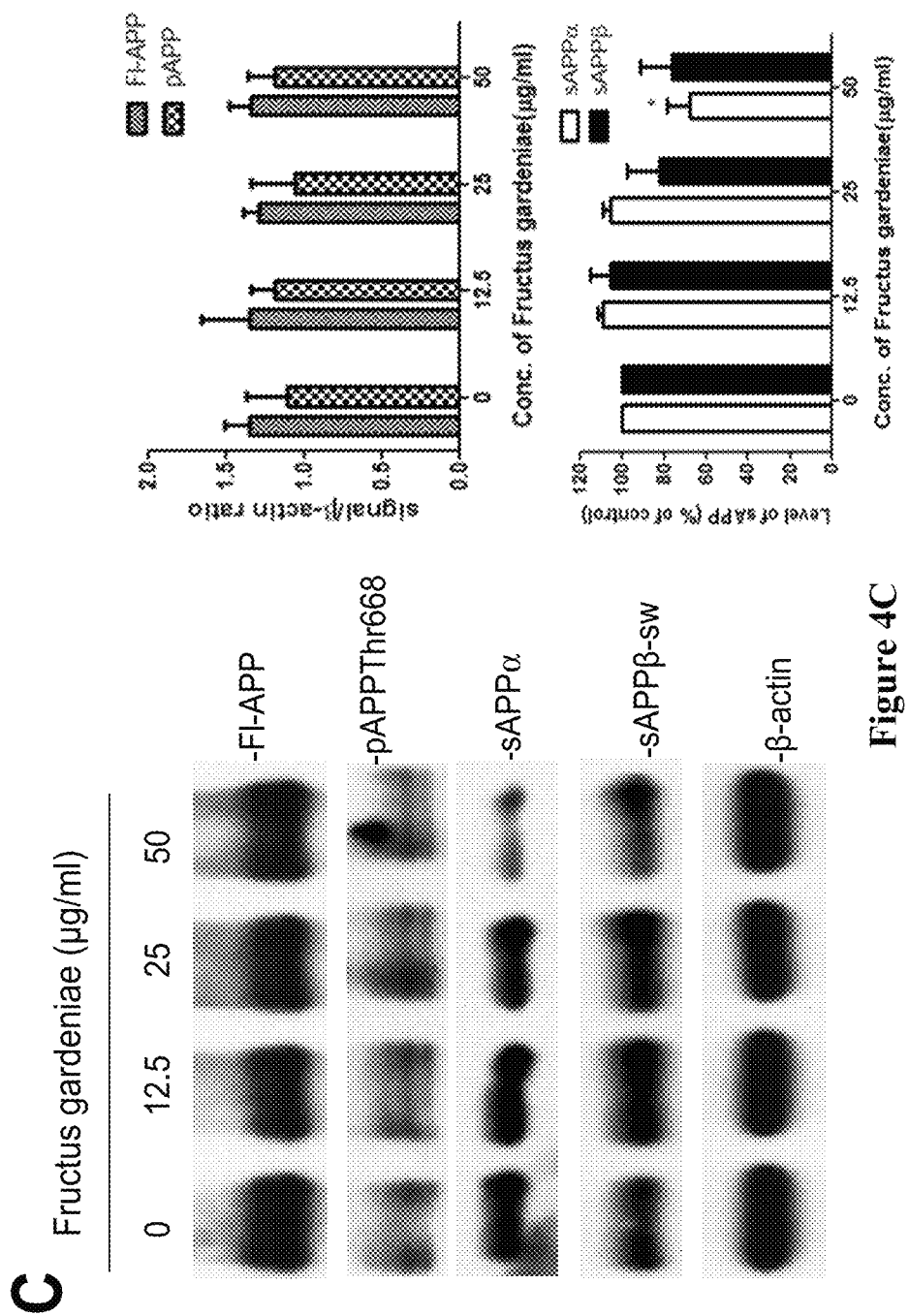
Figure 4D:
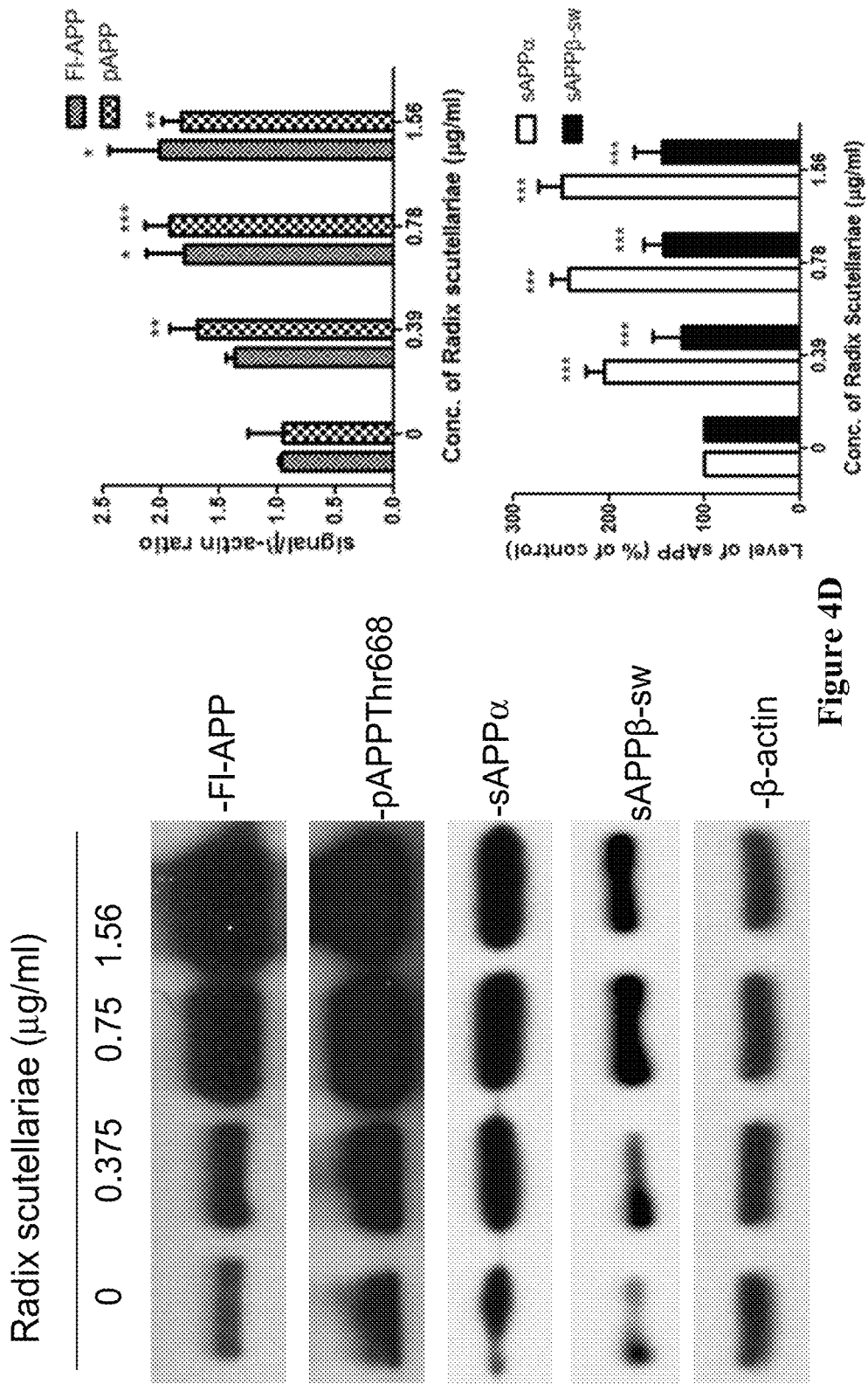

However, FG neither influences the level of F1-APP, nor does it affect pAPPThr668 metabolism; the only significant effect of FG is a slight decrease in sAPPα at a concentration of 50 µg/mL (FIG. 4C). In contrast with RC, CP and FG, RS significantly increases soluble APPs, intracellular APP and pAPPThr668 in a dose-dependent manner (FIG. 4D). The level of maximal stimulation of F1-APP and pAPPThr668 by RS is 1.89- and 2-fold of basal release, respectively, at a concentration of 1.56 µg/mL. The release of sAPPs is accelerated by treatment with RS in a dose dependent manner, reaching maximal augmentation at 1.4- and 2.4-fold of basal release for sAPPβ-sw and sAPPα, respectively, at a concentration of 1.56 µg/mL. These results demonstrate that the herbal components of HLJDT individually show differential modulation of APP processing.

Modulation of APP Processing by HLJDT and HLJDT-M

Figure 5A:
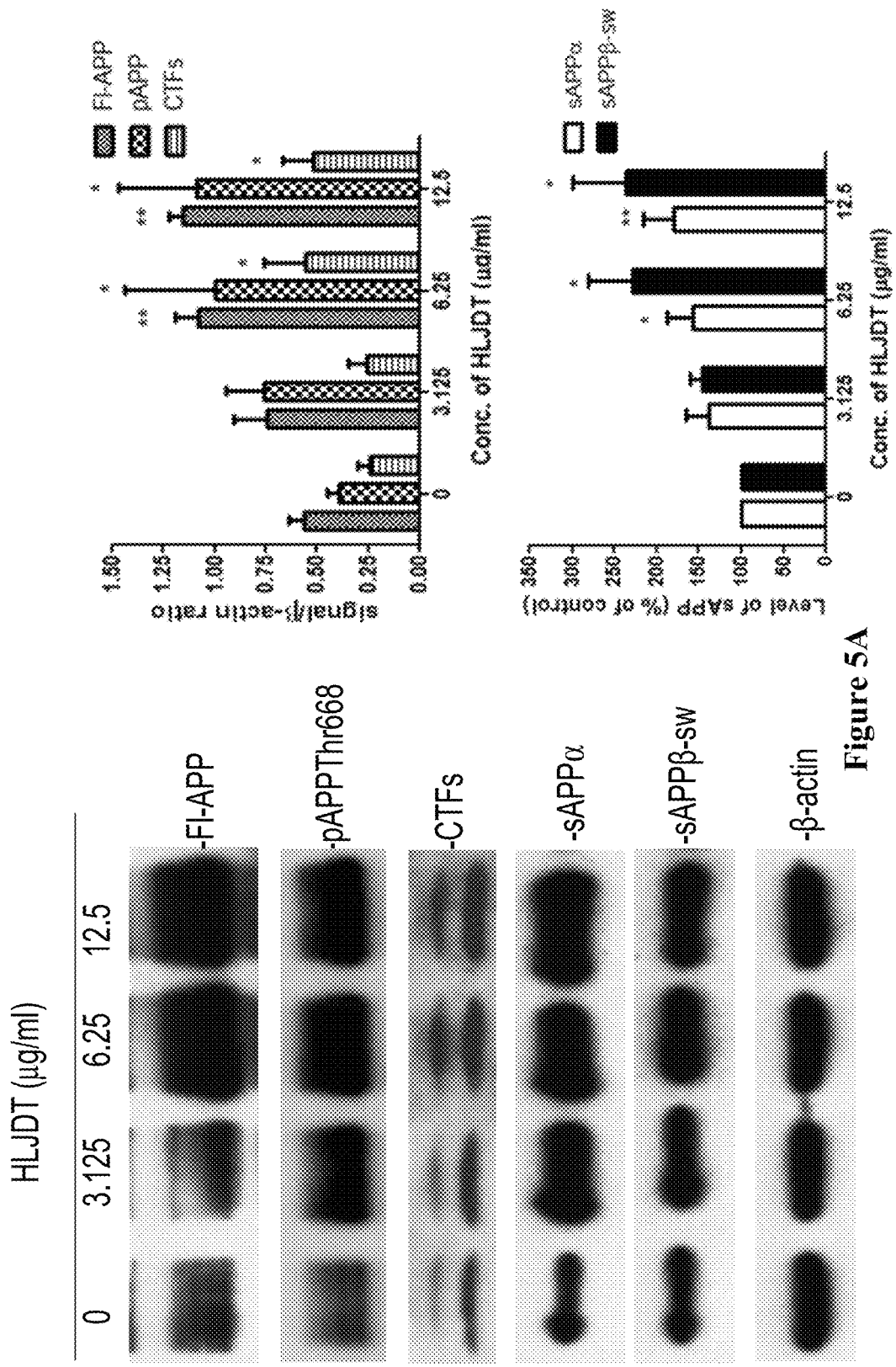
FIG. 5 shows the modulation of APP processing by HLJDT and HLJDT-M in N2a-SwedAPP cells. Conditioned medium and cell lysates were prepared from N2a-SwedAPP cells that were treated with HLJDT (FIG. 5A) or HLJDT-M (FIG. 5B) at various doses as indicated for 48 hours. Bars represent mean±S.E.M. for three experiments.

HLJDT significantly increases soluble APPs, intracellular APP, pAPPThr668 and CTFs in a dose-dependent manner (FIG. 5A). The level of maximal increase of F1-APP and pAPPThr668 by HLJDT is 2.0- and 2.8-fold of basal release, respectively, at a concentration of 12.5 µg/mL. HLJDT treatment not only increases the level of F1-APP and pAPPThr668 but also dose-dependently increases the generation of CTFs, confirming the APP-increasing effect of HLJDT. HLJDT increases CTFs to 2.1 and 2.3 times the basal levels at concentrations of 12.5 ($p<0.05$) and 6.25 ($p<0.05$) µg/mL, respectively. Accordingly, sAPPα and sAPPβ-sw are also elevated. The release of sAPPs is accelerated by treatment with HLJDT in a dose-dependent manner, reaching maximal augmentation at 2.4 and 1.4 fold of basal release for sAPPβ-sw and sAPPα, respectively, at a concentration of 12.5 µg/mL. The increase in sAPPs levels is consistent with the increase in F1-APP and CTFs levels by HLJDT, and indicates that HLJDT increases amyloidogenic processing of APP.

Figure 5B:
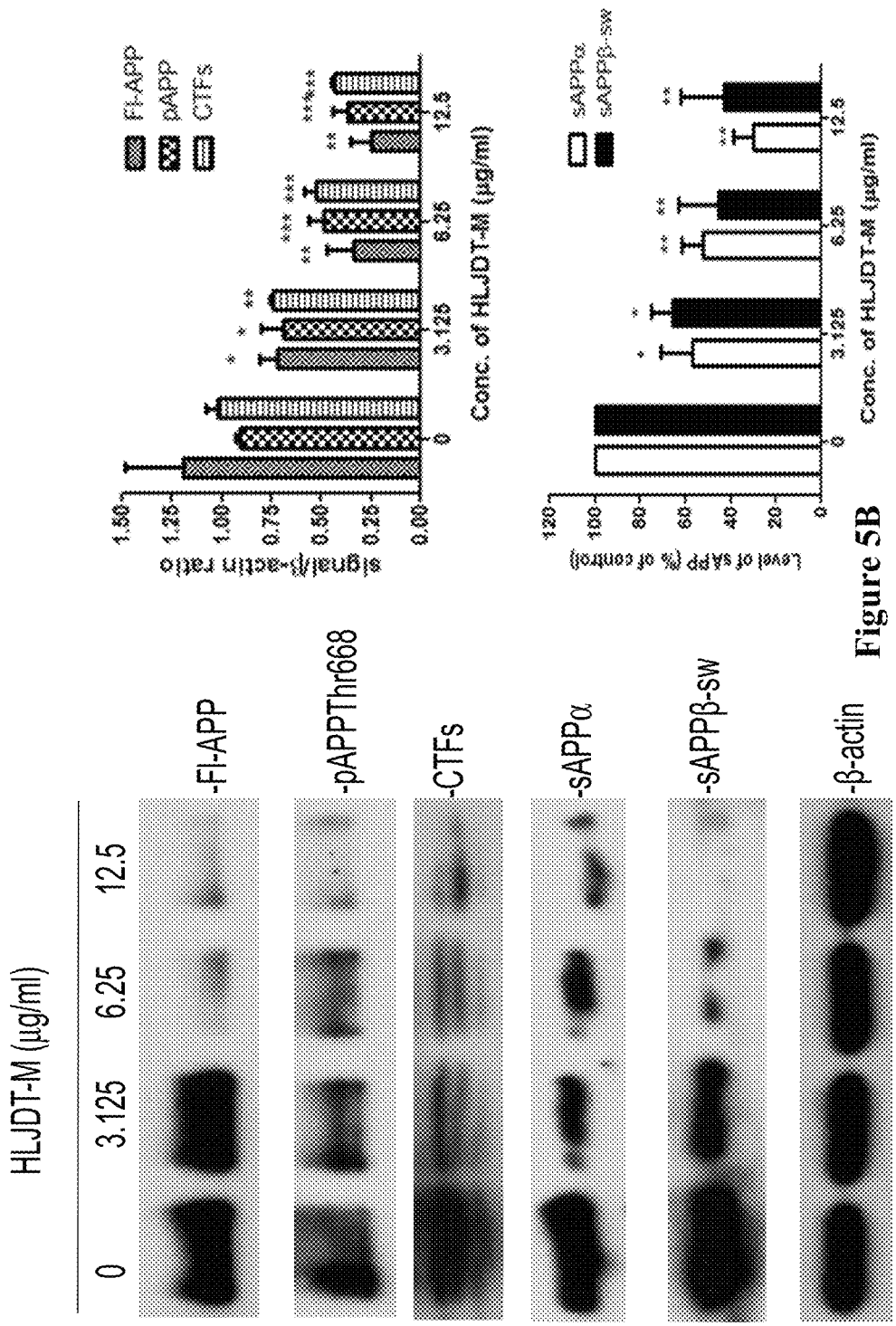

As demonstrated by the above studies of the present application, both RS and HLJDT increase APP metabolism, which are unfavorable for neural degenerative disease treatments On the other hand, the present invention provides a herbal composition comprising RC, CP and FG at a ratio of 4:2:4 and excluding RS. The present herbal composition significantly and dose-dependently decreases all metabolic products of APP to an even greater extent than RC and CP alone. The present herbal composition (HLJDT-M) treatment at a concentration of 12.5 µg/mL reduces the levels of F1-APP, pAPPThr668 and CTFs by 79% ($p<0.01$), 60% ($p<0.001$) and 68% ($p<0.001$), respectively (FIG. 5B). The levels of sAPPα and sAPPβ-sw are reduced by 70% ($p<0.001$) and 57% ($p<0.01$), respectively (FIG. 5B). Exclusion of RS of the present invention totally reverses the amyloidogenic property of HLJDT.

Modulation of APP Processing by Berberine and Baicalein

Figure 6A:
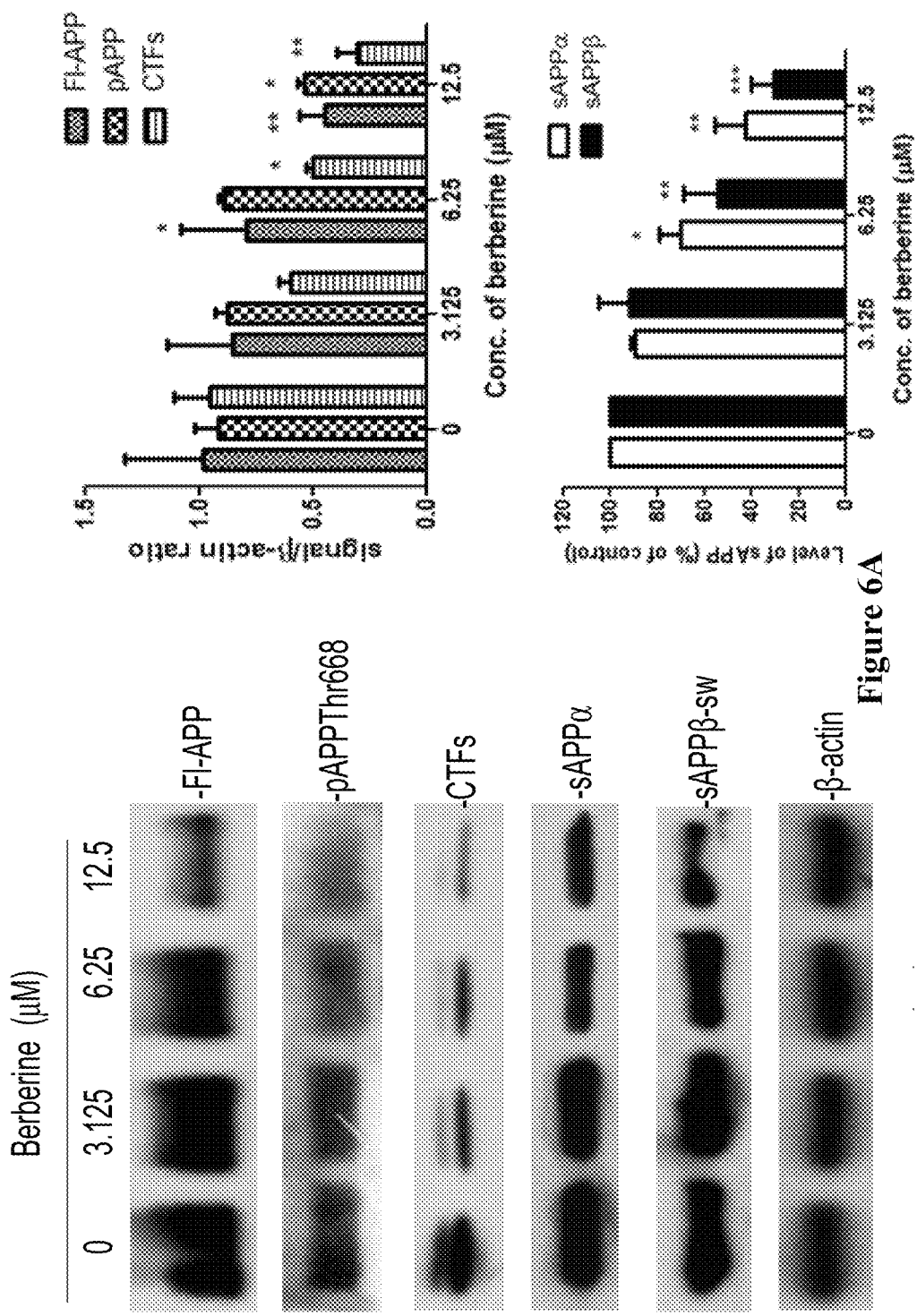
FIG. 6 shows the modulation of APP processing by berberine and baicalein in N2a-SwedAPP cells. Conditioned medium and cell lysates are prepared from N2a-SwedAPP cells that are treated with berberine (FIG. 6A) or baicalein (FIG. 6B) at various doses for 48 hours. Bars represent mean±S.E.M. for three experiments.
Figure 6B:
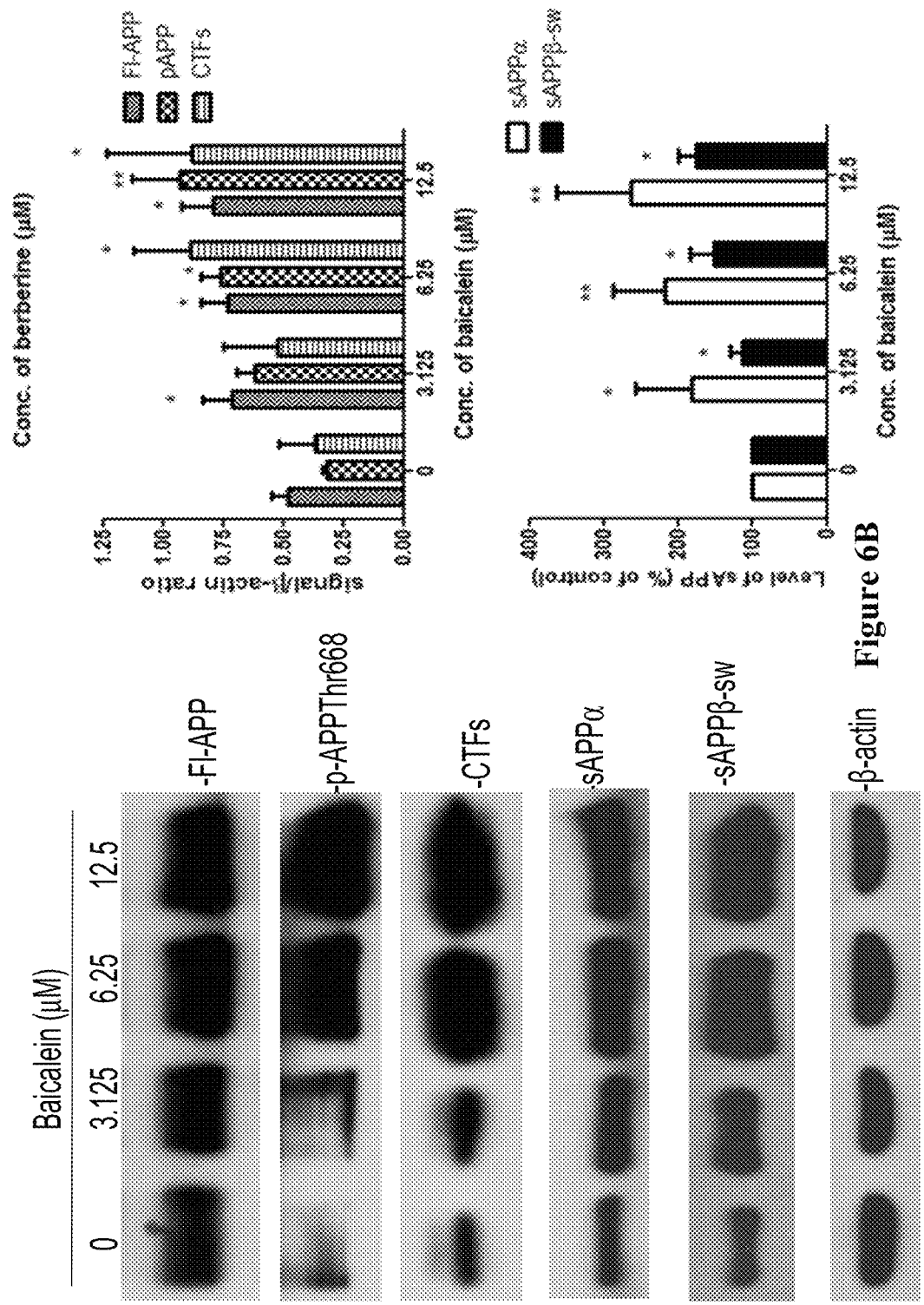

Berberine and baicalein have been extensively studied as markers for HLJDT, therefore the effects of these active components of HLJDT on APP metabolism were examined. It was determined herein that berberine significantly decreases Aβ, pAPPThr688 and CTFs in both in vivo and in vitro models of AD. The effect of berberine on APP metabolism in N2a-SwedAPP cells is assessed. Berberine significantly decreased soluble APPs, intracellular APP, pAPPThr668 and CTFs in a dose-dependent manner (FIG. 6A). Levels of sAPPα and sAPPβ-sw were reduced by 58% ($p<0.01$) and 70% ($p<0.001$), respectively, by treatment with 12.5 µM berberine, and by 30% ($p<0.05$) and 45% ($p<0.01$) by 6.25 µM berberine. Berberine treatment at a concentration of 12.5 µM reduced the level of F1-APP, pAPPThr668 and CTFs by 54% ($p<0.01$), 42% ($p<0.05$) and 67% ($p<0.01$), respectively. Since RS and HLJDT increase all APP metabolic products, whether baicalein alone can induce the same APP increasing effect as RS and HLJDT is investigated. Baicalein significantly increased soluble APPs, F1-APP, pAPPThr668 and CTFs in a dose-dependent manner (FIG. 6B). The levels of maximal increase of F1-APP, pAPPThr668 and CTFs by baicalein were 1.68 ($p<0.05$), 1.58 ($p<0.01$) and 2.36 ($p<0.05$) fold of basal release, respectively, at a concentration of 12.5 µM. The release of sAPPs was accelerated by treatment with baicalein in a dose-dependent manner, reaching maximal secretion of 2.65 ($p<0.01$) and 1.70 ($p<0.05$) fold of basal release for sAPPα and sAPPβ-sw, respectively, at a concentration of 12.5 µM. These data show that berberine is one of the alkaloids responsible for the APP-decreasing effect of HLJDT-M, and baiclein is one of the flavonoids responsible for the APP-increasing effect of HLJDT.

Figure 7A:
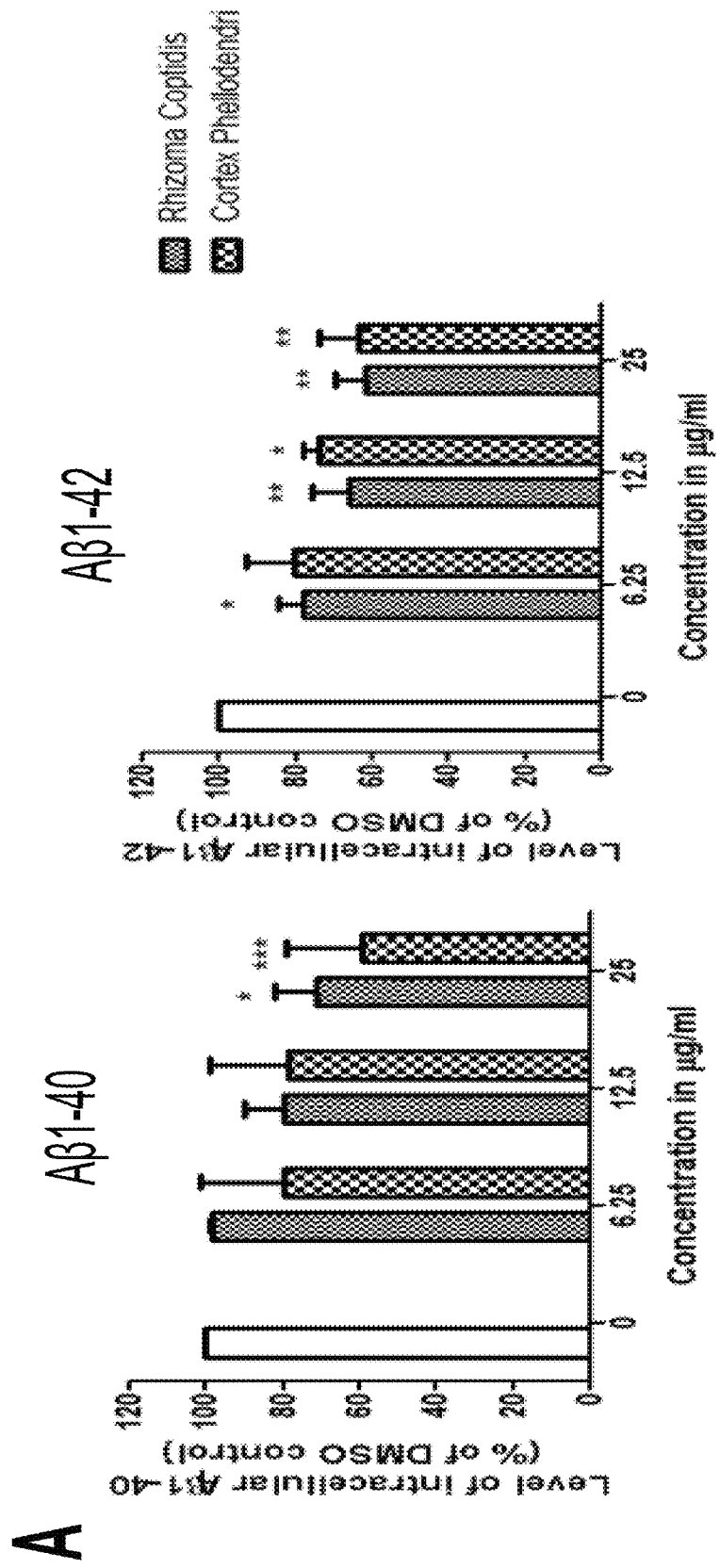
FIG. 7 shows the regulation of the levels of intracellular Aβ by HLJDT, HLJDT-M and extracts of HLJDT herbal components in cultured N2a-SwedAPP cells. Aβ1-40 and Aβ1-42 peptides are analyzed by enzyme-linked immunosorbent assay (ELISA) in N2a-SwedAPP cell lysates 48 h after addition of RC or CP (FIG. 7A); RS (FIG. 7B); HLJDT or HLJDT-M (FIG. 7C); and berberine or baicalein (FIG. 7D). Bars represent mean±S.E.M. of the level of intracellular Aβ1-40 or Aβ1-42 peptides in three experiments relative to DMSO control (untreated).
Figure 7B:
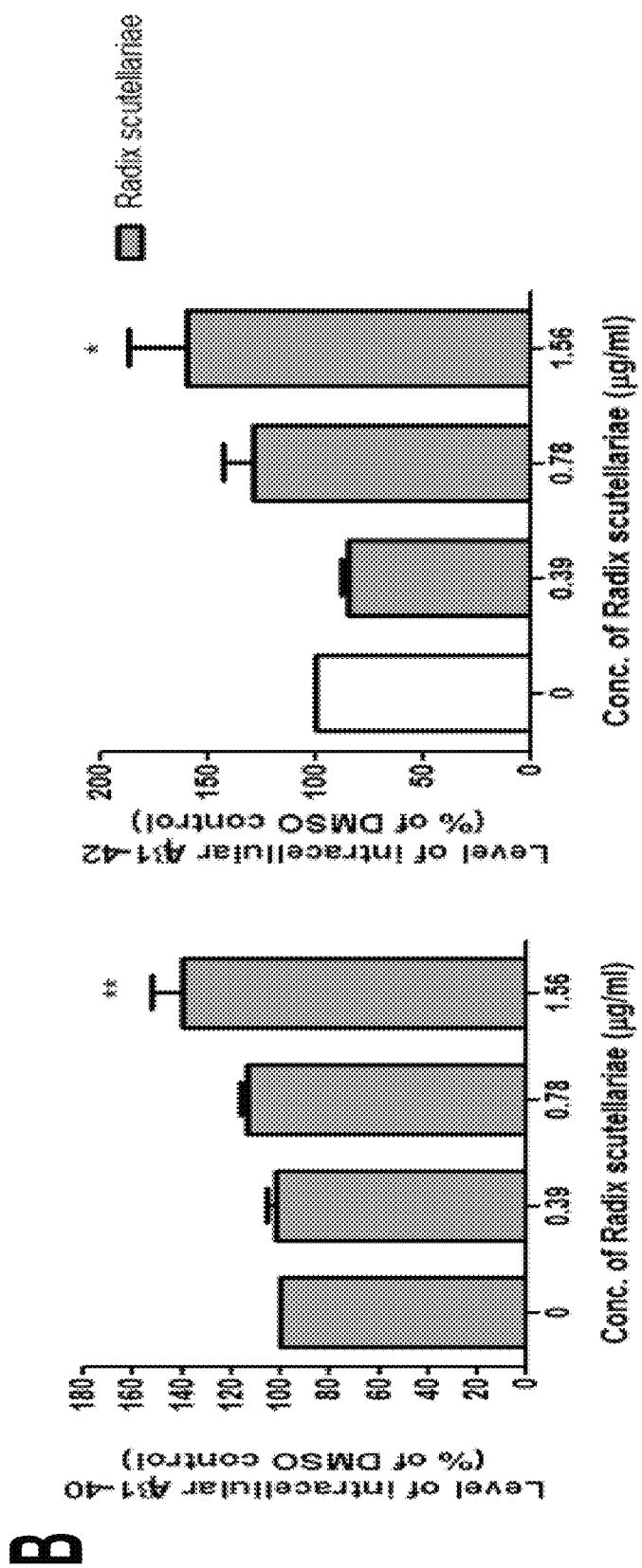

Modulation of Intracellular Aβ Levels by HLJDT, HLJDT-M and their Components in N2a-SwedAPP Cells Since HLJDT and its individual herbal components modulate intracellular levels of APP and CTFs in N2a-SwedAPP, the effect of HLJDT and its components on the level of intracellular Aβ, which is a key factor in AD progression is investigated. N2a-SwedAPP cells with different non-toxic concentrations of HLJDT, HLJDT-M and individual herbal components are tested and then analyzed intracellular Aβ levels by ELISA (FIG. 7A-7D). There is a dose-dependent reduction in both Aβ1-40 and Aβ1-42 by both RC and CP treatments. Intracellular Aβ1-40 markedly dropped 41% and 29% due to treatment by 25 µg/mL RC and CP, respectively (FIG. 7A). There was a 32% reduction in intracellular Aβ1-42 in both RC and CP treated cells at the same high concentration. In contrast, RS treatment increases intracellular Aβs in a dose-dependent manner, reaching maximal accumulation of 1.4- and 1.6-fold of basal levels of Aβ1-40 and Aβ1-42, respectively, at a concentration of 1.56 µg/mL (FIG. 7B).

Figure 7C:
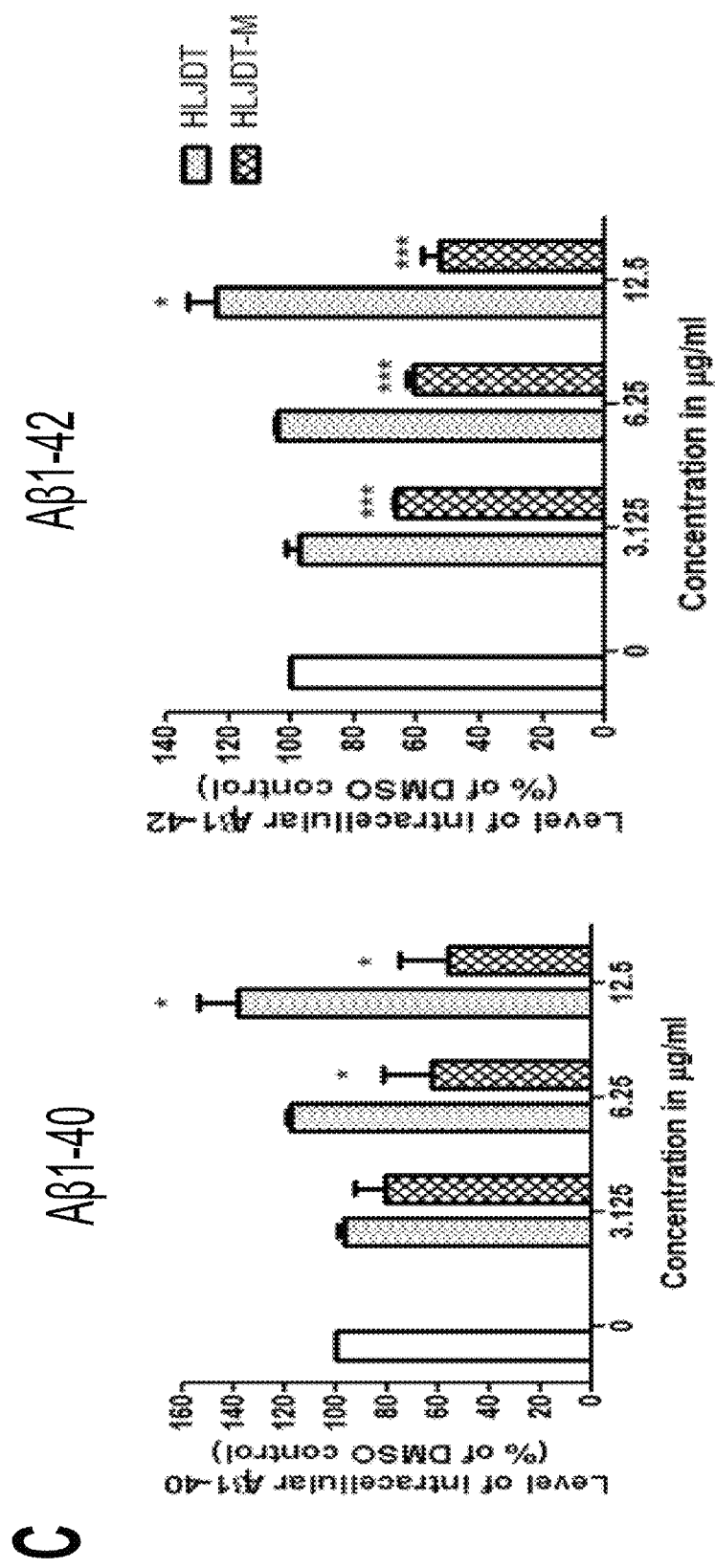
Figure 7D:
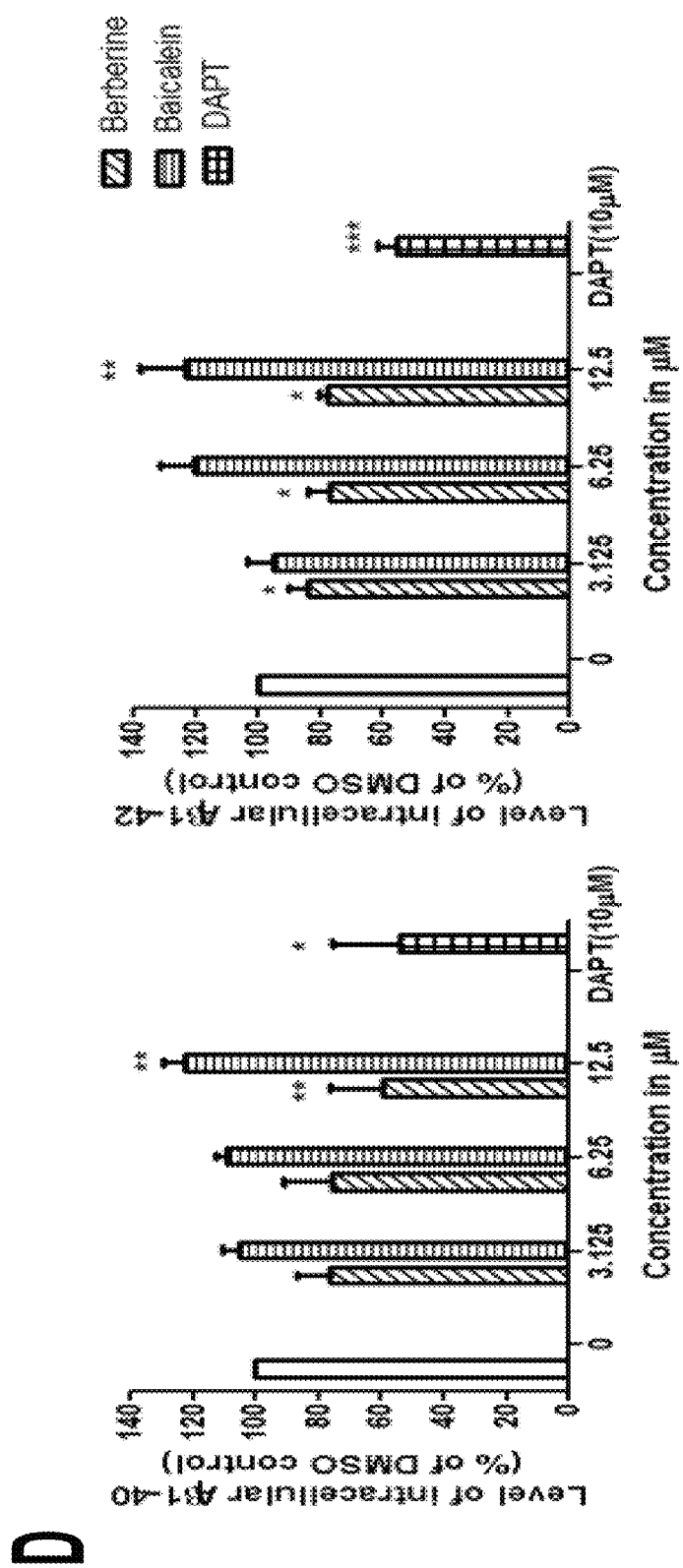

When comparing the effects of HLJDT and HLJDT-M on the level of intracellular Aβs, HLJDT increases both Aβ1-40 and Aβ1-42 in a dose-dependent manner, reaching maximal accumulation of 1.4- and 1.6-fold of basal level, respectively, at a concentration of 12.5 µg/mL (FIG. 7C). By contrast, HLJDT-M decreases both Aβ1-40 and Aβ1-42 in a dose-dependent manner. Intracellular Aβ1-40 markedly drops 44% with 12.5 µg/mL of HLJDT-M, 38% with 6.25 µg/mL and 20% with 3.125 µg/mL. Aβ1-42 is reduced 48% by 12.5 µg/mL of HLJDT-M, 39% with 6.25 µg/mL and 33% with 3.125 µg/mL (FIG. 7C). These data demonstrate that HLJDT-M, which lacks RS, significantly reduced intracellular Aβs, and that the Aβ-reducing effect is far more significant than that of the individual herbal components or HLJDT. Effects of berberine and baicalein are also studies. At a concentration of 12.5 µM, berberine significantly reduced both Aβ1-40 and Aβ1-42 by 37% and 25%, respectively, whereas baicalein significantly augments both Aβ1-40 and Aβ1-42 to 1.23 and 1.38 fold of basal level (FIG. 7D).

Figure 8A:
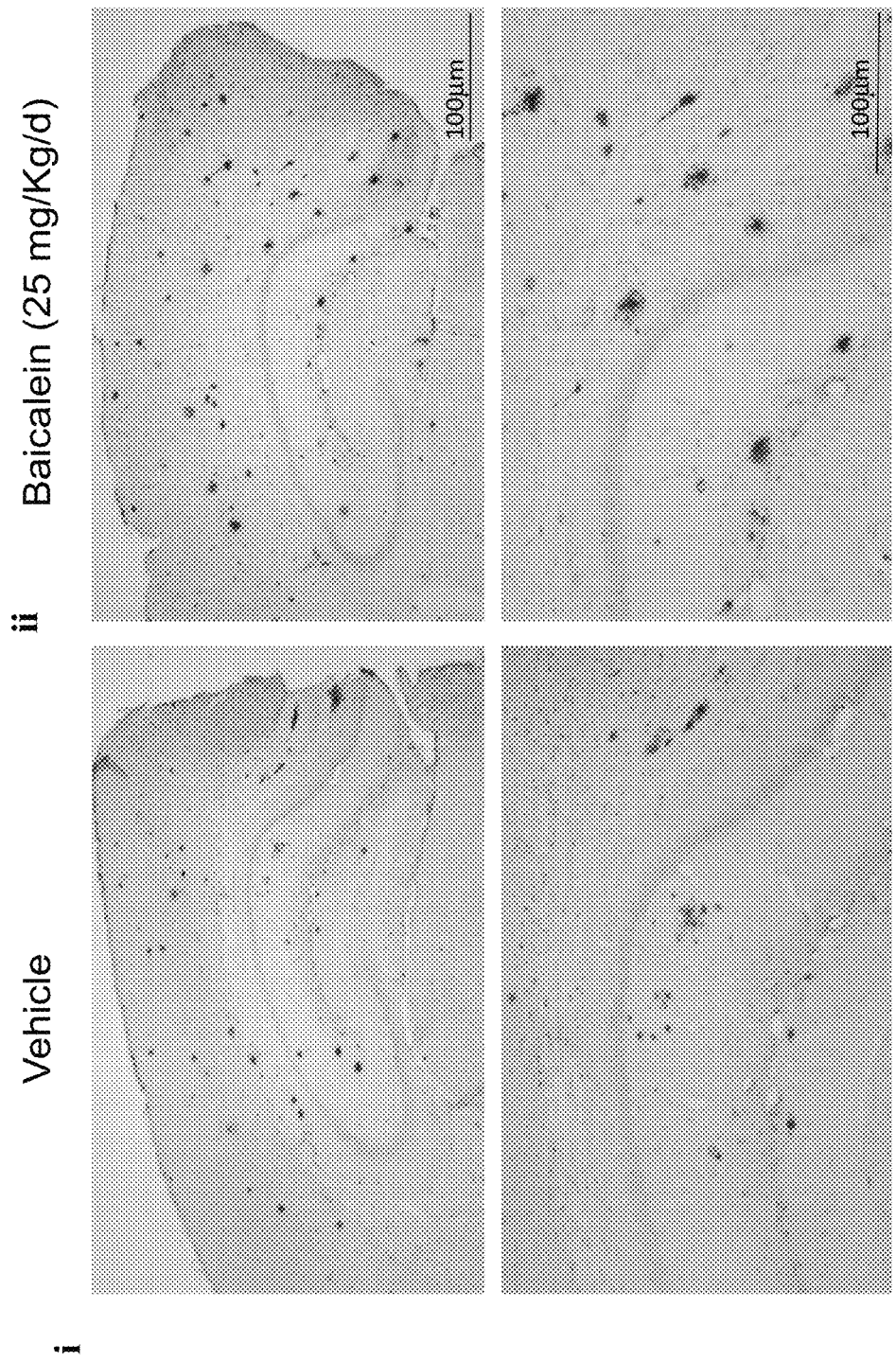
FIG. 8 shows baicalein increases cortico-hippocampal Aβ plaque pathology in TgCRND8 mice. Coronal sections of TgCRND8 mice treated with vehicle (FIG. 8A, i) or baicalein (FIG. 8A, ii) (25 mg/kg per day) and sacrificed after 3 months of treatment, followed by immunohistochemical staining for Aβ using 4G8 antibody. Scale bar: 100 μm. The percentage of coronal brain area occupied by Aβ immunoreactivity (FIG. 8B). Bars represent mean±S.E.M. for five mice per group.
Figure 8B:
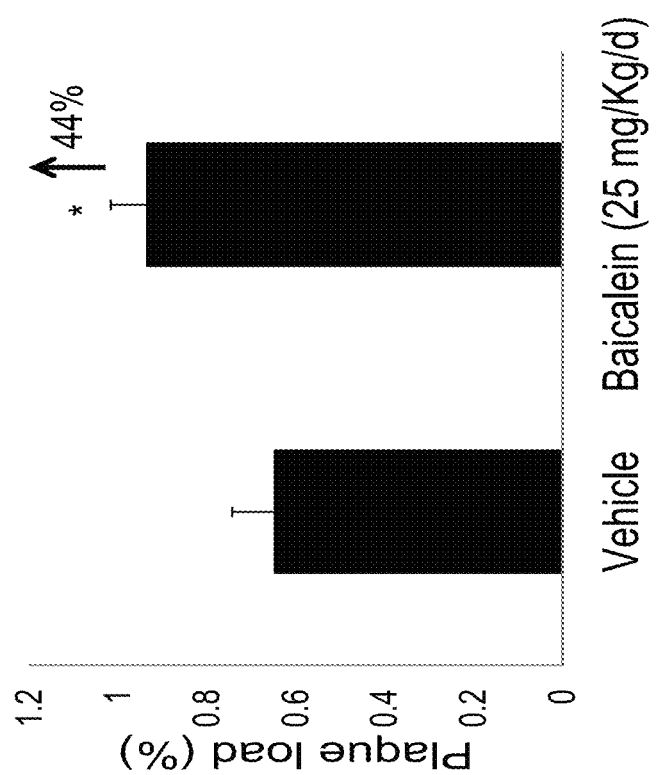

Chronic Baicalein Administration Increases Aβ Plaque Burden, Aβ Levels and Amyloidogenic APP Processing in TgCRND8 Mice In vivo efficacy of herbal components, the efficacy of berberine and baicalein, two widely studied compounds in HLJDT, are studied in a TgCRND8 mouse model of AD. Chronic administration of berberine can significantly reduce Aβ pathology, gliosis and cognitive impairments in TgCRND8 mice via reducing the level of C-terminal fragments of APP and the level of phosphorylated APP is shown. Baicalein treatment increased APP metabolites and intracellular Aβ in a cell culture study directed further examination on the effect of baicalein on Aβ plaque load in TgCRND8 mice. The present application shows that chronic oral administration of baicalein at 25 mg/kg per day for nearly 3 months did not significantly change animal body weight, nor did it cause any notable adverse side effects in TgCRND8 mice. Immunostaining of amyloid plaques in the brains of TgCRND8 mice revealed that baicalein treatment increased the area occupied by Aβ deposits in cortex and hippocampus by 44% ($p<0.05$) (FIGS. 8A and 8B).

Figure 9A:
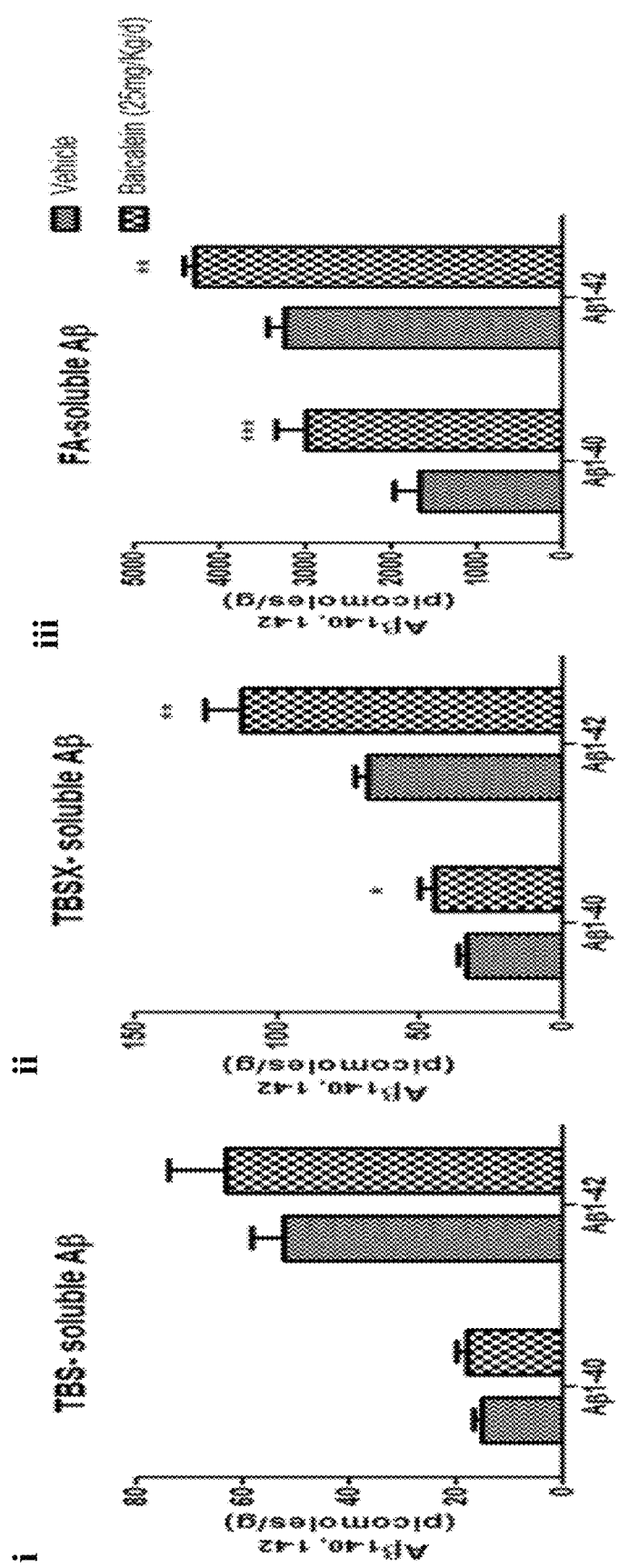
FIG. 9 shows baicalein treatment increases amyloidogenic processing in TgCRND8 mice. Serial extraction of TBS-soluble (FIG. 9A, i), TBSX-soluble (FIG. 9A, ii) and FA-soluble Aβ1-40 and Aβ1-42 (FIG. 9A, iii) from cerebral hemispheres of five vehicle-treated or five baicalein-treated (25 mg/kg per day) TgCRND8 mice, measured by sandwich ELISA. Immunoblots demonstrating the levels of sAPPs, F1-APP, pAPPThr668, CTFs and β-actin in TBS-extracted brain lysates (FIG. 9B, i) and TBSX-extracted brain lysates (FIG. 9B, ii) from the above mice. Densitometric analysis of the immunoblots, performed using Image J, with signals normalized to those for β-actin. Bars represent mean±S.E.M. for five mice per group. Student's t-test revealed a significant difference due to treatment: *$p<0.05$, **$p<0.01$.

The above results of increased 4G8-positive Aβ deposits by baicalein treatment are further ascertained by Aβ ELISA analysis in the other hemisphere of the brain. Aβ1-40 and Aβ1-42 levels in TBS, TBSX and FA brain fractions were measured via ELISA. Baicalein treatment did not significantly affect TBS soluble Aβ levels but significantly increase both TBSX-soluble and insoluble formic acid fractions (FIG. 9A, i, ii and iii). In the TBSX-soluble fraction, the increases of Aβ1-40 and 1-42 were 35% ($p<0.05$) and 65% ($p<0.01$), respectively, whereas in the FA fraction, the corresponding increases were 80% ($p<0.001$) and 32% ($p<0.01$).

Figure 9B:
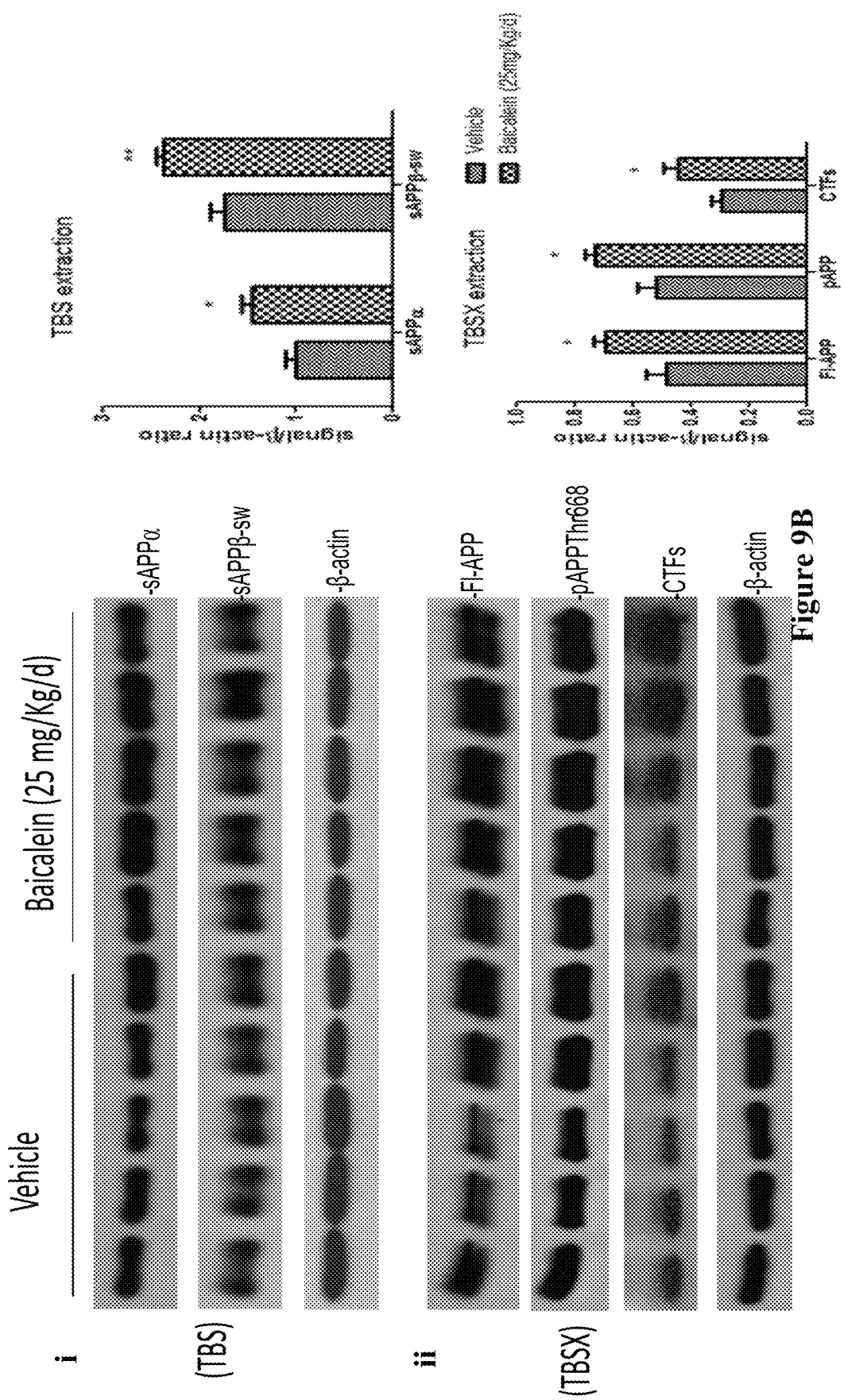

To examine the modulation of APP processing by baicalein treatment, serially extracted fractions are subjected to western blot analyses to specifically detect soluble and membrane associated APP. The TBS fraction was analyzed for sAPPα and sAPPβ-sw, and the TBSX fraction was analyzed for F1-APP, CTFs and pAPPThr668. Antibodies specific for sAPPβ-sw and sAPPα reveal increases in signal intensities of 35% ($p<0.01$) and 44% ($p<0.05$), respectively, after baicalein treatment (FIG. 9B, i). Immunoblot analysis also showed 30%, 40% and 41% increases in the levels of F1-APP, CTFs, and pAPP, respectively (FIG. 9B, ii). The increased metabolic products of APP following baicalein treatment in mice is also consistent with in vitro data that baicalein increases amyloidogenic processing of APP.

In summary, the clinical uses of HLJDT, which has been traditionally prescribed in China to treat gastrointestinal diseases, acute liver injury and cardiovascular diseases, have now been extended to treat patients with cerebrovascular diseases and vascular dementia in China and Japan. Pharmacological in vitro and in vivo studies have confirmed the neuroprotective activities of HLJDT against cerebrovascular diseases. Three single pure compounds (berberine, baicalein and genipiposide) from HLJDT show activities in different AD models. In the experimental plan primarily designed to identify key herbs and compounds responsible for the neuroprotective effects of HLJDT in an in vitro AD model, N2aSwedAPP cells, unexpectedly found in the present invention that RS alone and HLJDT instead strongly increased F1-APP, pAPPThr668, CTFs, sAPPs and Aβ (FIGS. 4D and 5A). The increased Aβ levels also translate into an increased amyloid plaque burden in a mouse model of Alzheimer's disease (FIGS. 8 and 9). In contrast, the herbal composition of the present invention comprising RC, CP and FG at the ratio of 4:2:4 significantly decreases all the APP metabolic products including Aβ (FIGS. 5B and 7C). The unexpected result of the present invention shows that RS is an anti-oxidative herb and its removal reduces the anti-oxidative capacity of HLJDT-M. The unexpected result also shows that FG and active compounds thereof have significant antioxidative and memory enhancing activity without influencing APP modulation. RC is shown to be the most active drug in HLJDT and has a significantly high amount of protoberberine alkaloids (e.g. palmatine). Based on these evidences, a composition comprises RC, CP and FG at a ratio of 4:2:4, excluding RS is provided in the present invention. It is shown herein that berberine can decrease both sAPPα and sAPPβ-sw, in addition to reducing Aβ, pAPPTh668 and CTFs accumulation (FIGS. 6A and 7D). Since sAPPα and sAPPβ-sw have recently been considered potential markers of AD, the sAPPs reducing effect of berberine adds to the evidence for its anti-AD effect. The herbal composition of the present invention shows more significant APP- and Aβ-reducing effects than berberine, RC or CP treatment alone. The greater APP and Aβ reducing effect of the present invention demonstrates synergistic action of related protoberberine alkaloids (coptisine, palmatine, jatterorhizine etc.) with berberine in the present composition. The overall influences of the present herbal composition, HLJDT and individual herbal components on APP metabolic products are shown in Table 3.

Table 3 shows The overall influence of HLJDT components on APP metabolic products

| Components | Fl-APP | pAPP | CTFs | sAPPα | sAPPβ | Aβs |
|---|---|---|---|---|---|---|
| RC | ↓ | ↓ | nd | ↓ | ↓ | ↓ |
| CP | ↓ | ↓ | nd | ↓ | ↓ | ↓ |
| FG | ↔ | ↔ | nd | ↔ | ↔ | nd |
| RS | ↑ | ↑ | nd | ↑ | ↑ | ↑ |
| HLJDT | ↑ | ↑ | ↑ | ↑ | ↑ | ↑ |
| HLJDT-M | ↓ | ↓ | ↓ | ↓ | ↓ | ↓ |
| Berberine | ↓ | ↓ | ↓ | ↓ | ↓ | ↓ |
| Baicalein | ↑ | ↑ | ↑ | ↑ | ↑ | ↑ |

↓ decreased,
↑ increased,
↔ unchanged,
nd not determined

It has been revealed in Lee M S, Kao S C, Lemere C A, Xia W, Tseng H C, Zhou Y, Neve R, Ahlijanian M K, Tsai L H (2003) APP processing is regulated by cytoplasmic phosphorylation. J Cell Biol 163: 83-95 that APP phosphorylation at position Thr668 accelerates the accumulation of CTFs and increases Aβ generation. Several studies such as da Cruz e Silva E F, da Cruz e Silva O A (2003) Protein phosphorylation and APP metabolism. Neurochem Res 28: 1553-1561 and Lee et al. 2003, have revealed that APP maturation and its targeting for proteolysis by secretases require APP Thr668 phosphorylation. The fast anterograde axonal transport of pAPPThr668 to the nerve terminals, where β- and α-secretase mediated cleavage occurs, results in increased Aβ release. This indicates that berberine-mediated reduction of APP phosphorylation might subsequently result in a reduction of mature pAPPThr668 and a reduced level of Fl-APP engaged in distal axons of neurons, which would prevent Aβ generation at synaptic terminals. Study on berberine of the present invention is in line with a previous study showing that lithium and JNK inhibitor peptide (D-JNKI1) reduce the Aβ burden mainly via reducing CTFs, pAPP and F1-APP without changing the level of BACE-1. In particular, D-JNKI1 has also been shown to reduce both sAPPα and β, similar to the present herbal composition, RC and their active compound berberine significantly reduces sAPPs.

It is believed the present invention is the first to show baicalein can potentiate Alzheimer's pathology both in vitro and in vivo (FIGS. 6B, 7D, 8 and 9). Baicalein's ability to increase APP, pAPPThr668 and CTFs as seen by Western analysis partially accounts for the increased Aβ generation (FIGS. 6B, 7D, 8 and 9). Baicalein enhances Aβ deposition is modulation of APP processing, because the levels of APP-CTFs, the direct precursor of Aβ, are increased by baicalein treatment (FIG. 6B). APP processing can be modulated in a number of ways, such as alterations in the function of β-secretase (BACE-1) or variation in APP transport. No significant change in the levels of BACE-1 protein (data not shown) is observed, thus baicalein may modulate APP processing through another mechanism. The phosphorylation of APP Thr-668 which is increased in the brain of AD patients is regulated by PIN 1 which may act as a conformational switch leading to altered APP turnover or maturation. The cis Thr-668-Pro conformation has been suggested to favor amyloidogenic processing. It is a conjecture of this application that baicalein or baicalein-containing HLJDT influences the PIN 1, which may alter the APP conformation. This will lead to an increase in sAPPs and thus increasing the Aβ generation. It is shown herein that baicalein treatment augments the abnormal processing of neuronal APP generating amyloidogenic fragments that, upon proteolysis, form Aβ. Similar to the study on the Aβ potentiating effect of baicalein in the present application, the anticancer drug cladribine and the proton-pump inhibitor lansoprazole have recently been shown in Hayes C D, Dey D, Palavicini J P, Wang H, Araki W, Lakshmana M K (2012) Chronic cladribine administration increases amyloid beta peptide generation and plaque burden in mice. PLoS ONE 7: e45841, and Badiola N, Alcalde V, Pujol A, Miinter L-M, Multhaup G, Lleó A, Coma M, Soler-López M, Aloy P (2013) The Proton-Pump Inhibitor lansoprazole enhances amyloid beta production. PLoS ONE 8: e58837 to significantly increase the generation of Aβ and amyloid plaques in cellular and animal models of AD. These Western drugs also significantly and dose dependently increased CTFs and sAPPs, in line with the studies of the present application that baicalein, RS and HLJDT mediated increases of APP metabolic products.

Although berberine and baicalein showed opposite effects on Aβ and are both components of HLJDT, the net effect of HLJDT increases Aβ load. Perhaps this is because baicalein (1-10 μM) has greater brain bioavailability than berberine Tsai T H, Liu S C, Tsai P L, Ho L K, Shum A Y, Chen C F. (2002) The effects of the cyclosporin A, a P-glycoprotein inhibitor, on the pharmacokinetics of baicalein in the rat: a microdialysis study. Br J Pharmacol 137: 1314-1320 and Durirajan et al. (2012). Only one pharmacokinetic study, which is Zhu H, Qian Z, He F, Liu M, Pan L, Zhang Q, Tang Y (2013) Novel pharmacokinetic studies of the Chinese formula Huang-Lian-Jie-Du-Tang in MCAO rats. Phytomedicine 20: 767-774, has reported the concentration of baicalein (quantity not shown) in rat brain after oral administration of HLJDT; the concentration is very low after a dose of 20 g/kg HLJDT (equivalent to 30 mg/kg baicalein). In the present invention, the mean concentration of baicalein in the brain of TgCRND8 mice is 0.12±0.01 μg/mL when orally administered at a concentration of 25 mg/kg. In the in vitro study of the present application, the highest Aβ-increasing concentration of baicalein in HLJDT (12.5 μg/mL) is 0.16 μg/mL, which is comparable to the effective in vivo concentration of baicalein. These findings indicate that baicalein can induce amyloidogenic activity in vivo. Although HLJDT is shown to be neuroprotective with memory enhancing activity in the ischemic model, the APP-increasing effect of baicalein may surpass its memory enhancing activity in AD models. The present invention determines for the first time that baicalein can potentiate Aβ not only in a cell culture model but also in an animal model of AD.

The present application provides convincing evidence for the first time that treatment HLJDT and its components RS or its active compound baicalein can increase amyloidogenic processing of APP in a cell model of AD. In addition, the chronic baicalein administration in TgCRND8 mice contributes to robustly increased plaque burden. Thus, chronic treatment of mice with baicalein or baicalein-containing HLJDT has deleterious effects in AD patients. The present herbal composition which excludes RS is a potent for AD therapy and improve memory deficit in AD patients because of the synergistic effect of berberine and other protoberberine alkaloids.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

INDUSTRIAL APPLICABILITY

This invention is in the field of pharmaceuticals, health supplements and chemical industries. The objective of the presently claimed invention is to provide a herbal composition that compensates the Aβ increasing effects of existing treatment, and on the regulatory processing of amyloid-β protein precursor (APP), therefore presenting a significantly more potent treatment for neurodegenerative diseases.

What we claim:

1. A method of treating a disease selected from the group consisting of Alzheimer's disease, taupathies, cerebreal amyloid angiopathy, dementia, neural mood, bipolar disorder, schizophrenia, Tourette's syndrome, and attention deficit hyperactivity disorder in a human in need thereof;
   wherein said human is administered a therapeutically effective amount of a composition consisting essentially of *Rhizoma coptidis* extract, *Cortex phellodendri* extract, and *Fructus gardenia* extract to effectively treat the Alzheimer's disease, taupathies, cerebreal amyloid angiopathy, dementia, neural mood, bipolar disorder, schizophrenia, Tourette's syndrome, or attention deficit hyperactivity disorder in said human.

2. The method according to claim 1, wherein each of said *Rhizoma coptidis, Cortex phellodendri*, and *Fructus gardenia* is an herb, an extract, an active ingredient thereof, or a combination thereof.

3. The method according to claim 2 wherein said extract is a water extract, an ethyl alcohol extract or an ethyl alcohol-water mixture extract.

4. The method according to claim 2, wherein said active ingredient of *Rhizoma coptidis* is palmatin, berberine or combination thereof, said active ingredient of *Cortex phellodendri* is palmatine, berberine or combination thereof, and said active ingredient of *Fructus gardenia* is geniposide.

5. The method according to claim 1, wherein weight ratio of said *Rhizoma coptidis, Cortex phellodendri* and *Fructus gardenia* is (3.5-4.5):(1.5-2.5):(3.5-4.5).

6. The method according to claim 1, wherein weight ratio of said *Rhizoma coptidis, Cortex phellodendri* and *Fructus gardenia* is (3.8-4.2):(1.8-2.2):(3.8-4.2).

7. The method according to claim 1, wherein weight ratio of said *Rhizoma coptidis, Cortex phellodendri* and *Fructus gardenia* is 4:2:4.

8. The method according to claim 1, wherein the composition diminishes generation, aggregation or deposition of amyloid-βpeptide in said human by inhibiting generation of soluble APPs, C-terminal fragments of APP or phosphorylation of APP and thereby treats said disease.

9. The method according to claim 1, wherein said composition is orally administered at 15-35 mg/kg/day for at least 3 months.

10. The method according to claim 9, wherein said composition is orally administered at 25 mg/kg/day for at least 3 months.

* * * * *